United States Patent
Wenk et al.

(10) Patent No.: US 9,109,051 B2
(45) Date of Patent: Aug. 18, 2015

(54) CROSSLINKED HYALURONIC ACID IN EMULSION

(75) Inventors: Hans Henning Wenk, Muelheim an der Ruhr (DE); Mike Farwick, Essen (DE); Sandra Nattland, Essen (DE); Ursula Maczkiewitz, Essen (DE); Birgitte Moelholm Malle, Birkeroed (DK)

(73) Assignees: EVONIK GOLDSCHMIDT GMBH, Essen (DE); NOVOZYMES BIOPOLYMER A/S, Bagsvaerd (DK)

( * ) Notice: Subject to any disclaimer, the term of this patent is extended or adjusted under 35 U.S.C. 154(b) by 804 days.

(21) Appl. No.: 12/809,809
(22) PCT Filed: Dec. 10, 2008
(86) PCT No.: PCT/EP2008/067172
§ 371 (c)(1), (2), (4) Date: Jun. 21, 2010
(87) PCT Pub. No.: WO2009/077399
PCT Pub. Date: Jun. 25, 2009

(65) Prior Publication Data
US 2010/0266512 A1 Oct. 21, 2010

Related U.S. Application Data

(60) Provisional application No. 61/015,261, filed on Dec. 20, 2007.

(30) Foreign Application Priority Data
Dec. 19, 2007 (EP) .................................... 07150176

(51) Int. Cl.
   *C08B 37/08* (2006.01)
   *A61K 8/37* (2006.01)
   (Continued)

(52) U.S. Cl.
   CPC ............. *C08B 37/0072* (2013.01); *A61K 8/025* (2013.01); *A61K 8/37* (2013.01);
   (Continued)

(58) Field of Classification Search
None
See application file for complete search history.

(56) References Cited

U.S. PATENT DOCUMENTS 4,478,853 A * 10/1984 Chaussee ....................... 514/772
4,582,865 A    4/1986 Balazs et al.
(Continued)

FOREIGN PATENT DOCUMENTS

DE    1165574      10/1964
DE    3740186 A1    1/1989
(Continued)

OTHER PUBLICATIONS

B Widner, R Behr, SV Dollen, M Tang, T Heu, A Sloma, D Sternberg, PL DeAngelis, PH Weigel, S Brown. "Hyaluronic Acid Production in *Bacillus subtilis*." Applied and Environmental Microbiology, vol. 71 No. 7, Jul. 2005, pp. 3747-3752.*

(Continued)

*Primary Examiner* — Isaac Shomer
(74) *Attorney, Agent, or Firm* — Scully, Scott, Murphy & Presser, P.C.

(57) ABSTRACT

The present invention relates to methods of producing crosslinked hyaluronic acid microbeads, as well as the produced microbeads, said method comprising the steps of: (a) providing an aqueous alkaline solution comprising hyaluronic acid, or a salt thereof; (b) forming microdroplets having a desired size from the mixed solution of step (a) in an organic or oil phase to form a water in organic or water in oil (VWO) emulsion, wherein the amount of oil phase used is of from 20 to less than 50% by weight based on the sum of oil phase and water; (c) adding a solution comprising a crosslinking agent to the emulsion, whereby the reaction of hyaluronic acid with the crosslinking agent takes place to provide crosslinked hyaluronic acid microbeads; and (d) optionally working up the dispersion of crosslinked hyaluronic acid microbeads obtained in step (c).

20 Claims, 5 Drawing Sheets

(51) Int. Cl.
*A61K 8/60* (2006.01)
*A61K 8/73* (2006.01)
*A61K 8/894* (2006.01)
*A61Q 19/08* (2006.01)
*C08J 3/07* (2006.01)
*C08J 3/26* (2006.01)
*C08L 5/08* (2006.01)
*A61K 8/02* (2006.01)

(52) U.S. Cl.
CPC ............... *A61K 8/375* (2013.01); *A61K 8/608* (2013.01); *A61K 8/735* (2013.01); *A61K 8/894* (2013.01); *A61Q 19/08* (2013.01); *C08J 3/07* (2013.01); *C08J 3/26* (2013.01); *C08L 5/08* (2013.01); *C08J 2305/08* (2013.01); *Y10T 428/2982* (2015.01)

(56) References Cited

U.S. PATENT DOCUMENTS

| | | | |
|---|---|---|---|
| 4,713,448 | A | 12/1987 | Balazs et al. |
| 4,801,539 | A | 1/1989 | Akasaka et al. |
| 4,957,744 | A | 9/1990 | della Valle et al. |
| 5,017,229 | A | 5/1991 | Burns et al. |
| 5,891,701 | A | 4/1999 | Sloma et al. |
| 6,013,679 | A | 1/2000 | Kuo et al. |
| 6,214,331 | B1 * | 4/2001 | Vanderhoff et al. ........ 424/78.17 |
| 6,242,499 | B1 * | 6/2001 | Gruning et al. ............... 514/785 |
| 2003/0175902 | A1 | 9/2003 | Sloma et al. |
| 2005/0031570 | A1 * | 2/2005 | Grit et al. ..................... 424/70.31 |
| 2005/0119219 | A1 * | 6/2005 | Bellini et al. ................... 514/54 |
| 2006/0040892 | A1 * | 2/2006 | Hu et al. ......................... 514/54 |

FOREIGN PATENT DOCUMENTS

| | | |
|---|---|---|
| DE | 4009347 A1 | 9/1991 |
| DE | 3938140 C2 | 1/1992 |
| DE | 4204321 A1 | 8/1993 |
| DE | 4229707 A1 | 3/1994 |
| DE | 4238081 C2 | 5/1995 |
| DE | 4324219 C2 | 8/1995 |
| DE | 4229737 C2 | 4/1996 |
| DE | 4309372 C2 | 8/1997 |
| DE | 19855934 A1 | 6/2000 |
| EP | 0161887 B1 | 9/1991 |
| EP | 0694616 A2 | 1/1996 |
| EP | 0694616 A3 | 1/1996 |
| EP | 0666732 B1 | 1/1997 |
| EP | 0830416 B1 | 8/2005 |
| EP | 1683812 A1 | 7/2006 |
| WO | WO9639464 | 12/1996 |
| WO | WO9822598 | 5/1998 |
| WO | WO9923227 | 5/1999 |
| WO | WO9951265 | 10/1999 |
| WO | WO0027437 A3 | 5/2000 |
| WO | WO0160868 A1 | 8/2001 |
| WO | WO03054163 A2 | 7/2003 |
| WO | WO03054163 A3 | 7/2003 |
| WO | WO03089476 A1 | 10/2003 |
| WO | WO2004067575 | 8/2004 |
| WO | WO2006056204 A1 | 6/2006 |
| WO | WO2008100044 A1 | 8/2008 |

OTHER PUBLICATIONS

Sahiner, N. et al., "One-Step Synthesis of Hyaluronic Acid-Based (Sub)micron Hydrogel Particles: Process Optimization and Preliminary Characterization", Turk J. Chem, 2008, 32, pp. 397-409.

"Kosmetische Färbemittel [Cosmetic Coloring Agents]" of the Dyestuffs Commission of the Deutsche Forschungsgemeinschaft, Verlag Chemie, Weinheim, 1984, pp. 81 to 106.

Finkel, P., "Formulierung kosmetischer Sonnenschutxmittel", SÖFW-Journal 1996, 122, p. 543, with English language abstract.

Ferretti, J. J., et al.,"Complete genome sequence of an M1 strain of *Streptococcus pyogenes*" Proc. Natl. Acad. Sci. USA., 2001, vol. 8, No. 8, pp. 4658-4663.

Deangelis, P. L., "Hyaluronan synthases: fascinating glycosyltransferases from vertebrates, bacterial pathogens, and algal viruses", Cell. Mol. Life Sci., 1999, 56, pp. 670-682.

Bitter, T., et al., "A Modified Uronic Acid Carbazole Reaction", Anal. Biochem., 1962, 4, pp. 330-334.

Ueno, Y., et al., "Low-Angle Laser Light Scattering Measurements on Highly Purified Sodium Hyaluronate from Rooster Comb", Chem. Pharm. Bull., 1988, 36, pp. 4971-4975.

Wyatt, P. J., "Light scattering and the absolute characterization of macromolecules", Anal. Chim. Acta, 1993, 272, pp. 1-40.

International Search Report dated Mar. 27, 2009.

* cited by examiner

CROSSLINKED HYALURONIC ACID IN EMULSION

CROSS REFERENCE TO RELATED APPLICATION

This application is a 371 of PCT/EP2008/067172 filed on Dec. 10, 2008 which claims the benefit of priority of European Patent Application No. 07 15 0176.1 filed on Dec. 19, 2007 and U.S. Provisional Patent Application Ser. No. 61/015,261, filed Dec. 20, 2007, the entire content and disclosure of which is incorporated herein by reference.

FIELD OF THE INVENTION

The present invention relates to a method of producing crosslinked hyaluronic acid microbeads, said method comprising the steps of:
(a) providing an aqueous alkaline solution comprising hyaluronic acid, or a salt thereof;
(b) forming microdroplets having a desired size from the mixed solution of step (a) in an organic or oil phase to form a water in organic or water in oil (W/O) emulsion, wherein the amount of oil phase used is of from 20 to less than 50% by weight based on the sum of oil phase and water;
(c) adding a solution comprising a crosslinking agent to the emulsion continuously stirring the W/O emulsion, whereby the reaction of hyaluronic acid with the crosslinking agent takes place to provide crosslinked hyaluronic acid microbeads; and
(d) optionally working up the dispersion of crosslinked hyaluronic acid microbeads obtained in step (c).

BACKGROUND OF THE INVENTION

The present invention relates to a process for the preparation of modified hyaluronic acid (HA), in particular crosslinked HA in emulsion, for use in cosmetic and personal care applications.

Hyaluronic acid (HA) is a natural and linear carbohydrate polymer belonging to the class of the non-sulfated glycosaminoglycans. It is composed of beta-1,3-N-acetyl glucosamine and beta-1,4-glucuronic acid repeating disaccharide units with a molecular weight (MW) up to 6 MDa. HA is present in hyaline cartilage, synovial joint fluid, and skin tissue, both dermis and epidermis. HA may be extracted from natural tissues including the connective tissue of vertebrates, from the human umbilical cord and from cocks' combs. However, it is preferred today to prepare it by microbiological methods to minimize the potential risk of transferring infectious agents, and to increase product uniformity, quality and availability (WO 03/0175902, Novozymes).

Numerous roles of HA in the body have been identified. It plays an important role in the biological organism, as a mechanical support for the cells of many tissues, such as the skin, tendons, muscles and cartilage. HA is involved in key biological processes, such as the moistening of tissues, and lubrication. It is also suspected of having a role in numerous physiological functions, such as adhesion, development, cell motility, cancer, angiogenesis, and wound healing. Due to the unique physical and biological properties of HA (including viscoelasticity, biocompatibility, biodegradability), HA is employed in a wide range of current and developing applications within cosmetics, opthalmology, rheumatology, drug delivery, wound healing and tissue engineering. The use of HA in some of these applications is limited by the fact that HA is soluble in water at room temperature, i.e. about 20° C., it is rapidly degraded by hyaluronidase in the body, and it is difficult to process into biomaterials. Crosslinking of HA has therefore been introduced in order to improve the physical and mechanical properties of HA and its in vivo residence time.

U.S. Pat. No. 4,582,865 (Biomatrix Inc.) describes the preparation of crosslinked gels of HA, alone or mixed with other hydrophilic polymers, using divinyl sulfone (DVS) as the crosslinking agent. The preparation of a crosslinked HA or salt thereof using a polyfunctional epoxy compound is disclosed in EP 0 161 887 B1. Other bi- or poly-functional reagents that have been employed to crosslink HA through covalent linkages include formaldehyde (U.S. Pat. No. 4,713,448, Biomatrix Inc.), polyaziridine (WO 03/089476 A1, Genzyme Corp.), L-aminoacids or L-aminoesters (WO 2004/067575, Biosphere S.P.A.). Carbodiimides have also been reported for the crosslinking of HA (U.S. Pat. No. 5,017,229, Genzyme Corp.; U.S. Pat. No. 6,013,679, Anika Research, Inc). Total or partial crosslinked esters of HA with an aliphatic alcohol, and salts of such partial esters with inorganic or organic bases, are disclosed in U.S. Pat. No. 4,957,744. Crosslinking of HA chains with 1-ethyl-3-(3-dimethylaminopropyl) carbodiimide hydrochloride ("EDAC") and adipic acid dihydrazide in a water/acetone mixture was disclosed in US 2006/0040892 (University of North Texas). WO 2006/56204 (Novozymes A/S) also discloses methods for the preparation of crosslinked gels of HA using divinyl sulfone (DVS) as the crosslinking agent.

WO 2008/100044 describes a method of preparing hyaluronic hydrogel nanoparticles by crosslinking hyaluronic acid, the method comprising mixing i) an oil phase containing a surfactant dissolved therein with ii) a water phase, containing hyaluronic acid and a water-soluble crosslinker, dissolved in an aqueous basic solution, so as to a form a w/o emulsion, and crosslinking the hyaluronic acid in the w/o emulsion, the oil phase comprising dodecane, heptane or cetylethylhexanoate.

EP 0 830 416 (equivalent of U.S. Pat. No. 6,214,331) describes the preparation of a crosslinked water-soluble polymer particle preparation wherein the particles are less than 212 μm in diameter and wherein at least 80% of the particles are spherical, obtainable by adding an aqueous polymer solution, comprising a water-soluble polymer selected from hyaluronic acid, chondroitin sulfate, dermatan sulfate, keratan sulfate, celluloses, chitin, chitosan, agarose, carrageenans, curdlan, dextrans, emulsan, gellan, xanthans, poly(ethyleneoxide), poly(vinyl alcohol), poly(N-vinyl pyrrolidone), proteins, glycoproteins, peptidoglycans, proteoglycans, lipopolysaccharides, or combinations thereof, and an aqueous medium, to an oil base containing a water in oil emulsifying agent, agitating the mixture to form an emulsion containing polymer droplets, and crosslinking the polymer droplets in situ by a crosslinking agent resulting in the formation of crosslinked polymer particles. For the production of hyaluronic acid microspheres the crosslinking agent is added directly to an emulsion of aqueous hyaluronic acid in toluene. The crosslinking agent is first deactivated by adjusting the pH of the aqueous solution to pH 11 and then activated by lowering the pH to 7 to 8. It is preferred to use toluene, o-xylene or isooctane as oil phase. The weight ratio of aqueous phase to oil phase is about 1 to 1.

Nurettin Sahiner and Xinqiao Jai (Turk J Chem, 32 (2008), 397-409) describe the preparation of hyaluronic acid based submicron hydrogel particles using isooctane as oil phase. For preparing the emulsion 0.54 ml of aqueous hyaluronic acid solution was added to 15 ml of isooctane, resulting in a weight ratio of aqueous phase to oil phase is higher then 10 to 1.

SUMMARY OF THE INVENTION

It is clear from the above, that several processes for preparing crosslinked HA-microbeads are known. Some of the components used as oil phase in the known processes are not qualified to be used as components in cosmetic or personal care compositions. Large amount of water or oil phase are used to produce the microbeads. There is therefore a need to provide an alternative method to prepare crosslinked microbeads that does not show one or more of the disadvantages of the known methods.

Surprisingly we found that a method of producing crosslinked hyaluronic acid microbeads, said method comprising the steps of:
(a) providing an aqueous alkaline solution comprising hyaluronic acid, or a salt thereof;
(b) forming microdroplets having a desired size from the mixed solution of step (a) in an organic or oil phase to form a water in organic or water in oil (W/O) emulsion, wherein the amount of oil phase used is of from 20 to less than 50% by weight based on the sum of oil phase and water;
(c) adding a solution comprising a crosslinking agent to the emulsion continuously stirring the W/O emulsion, whereby the reaction of hyaluronic acid with the crosslinking agent takes place to provide crosslinked hyaluronic acid microbeads; and
(d) optionally working up the dispersion of crosslinked hyaluronic acid microbeads obtained in step (c),
solves the problems known from the methods of the prior art.

The method of the invention has the advantage that a minimum of waste water or waste oil phase is produced. By using emollients accepted for personal care or cosmetic use the resulting microbeads of the invention do not show any skin irritation problems that might occur when using hydrocarbons as emollient. The process of the invention has the advantage, that there is no need to completely remove the components used as oil phase from the microbeads before forming the cosmetic or personal care formulations. It is even possible to directly use the dispersions obtained from step (c) with or without being subsequently neutralized.

Accordingly, in a first aspect the invention provides a method of producing crosslinked hyaluronic acid microbeads, said method comprising the steps of:
(a) providing an aqueous alkaline solution comprising hyaluronic acid, or a salt thereof;
(b) forming microdroplets having a desired size from the mixed solution of step (a) in an organic or oil phase to form a water in organic or water in oil (W/O) emulsion, wherein the amount of oil phase used is of from 20 to less than 50% by weight based on the sum of oil phase and water;
(c) adding a solution comprising a crosslinking agent to the emulsion continuously stirring the W/O emulsion, whereby the reaction of hyaluronic acid with the crosslinking agent takes place to provide crosslinked hyaluronic acid microbeads; and
(d) optionally working up the dispersion of crosslinked hyaluronic acid microbeads obtained in step (c).

In a second aspect, the invention relates to microbeads comprising hyaluronic acid, or salt thereof, crosslinked preferably with divinylsulfone. Those microbeads are preferably made or obtained by the method of the first aspect.

In a third aspect, the invention relates to a composition comprising microbeads as defined in the second aspect.

A fourth aspect of the invention relates to the use of microbeads according to the second aspect of the invention or a composition according to the third aspect of the invention or a dispersion obtained by a method according to the first aspect of the invention for the manufacture of a moisturizer, a personal care, a hair care, a skin care or a cosmetic composition.

Other aspects of the invention relate to personal care compositions comprising an (effective amount) of microbeads as defined in the second aspect as a vehicle, together with a personal care active agent, preferably encapsulated in the microbead, cosmetic articles comprising as an active ingredient an effective amount of a microbead as defined in the second aspect or a composition as defined in the third, sanitary articles comprising a microbead as defined in the second aspect or a composition as defined in the third aspect, preferably the article is a diaper, a sanitary towel, a surgical sponge, a wound healing sponge, or a part comprised in a band aid or other wound dressing material.

A number of aspects relate to uses of a microbead as defined in the second aspect or a composition as defined in the third aspect, for the manufacture of the manufacture of a moisturizer or a cosmetic, or in a cosmetic treatment.

BRIEF DESCRIPTION OF DRAWINGS

FIG. 1 shows a microscope picture of a dispersion obtained according to example 2. The spherical character of the microbeads (particles) can be seen.

FIG. 2 shows a graph of the particle size distribution of the particles obtained in example 2.

FIG. 3 shows a microscope picture of a pig skin. The pig skin was treated according to example 7.

DEFINITIONS

Figure 1:
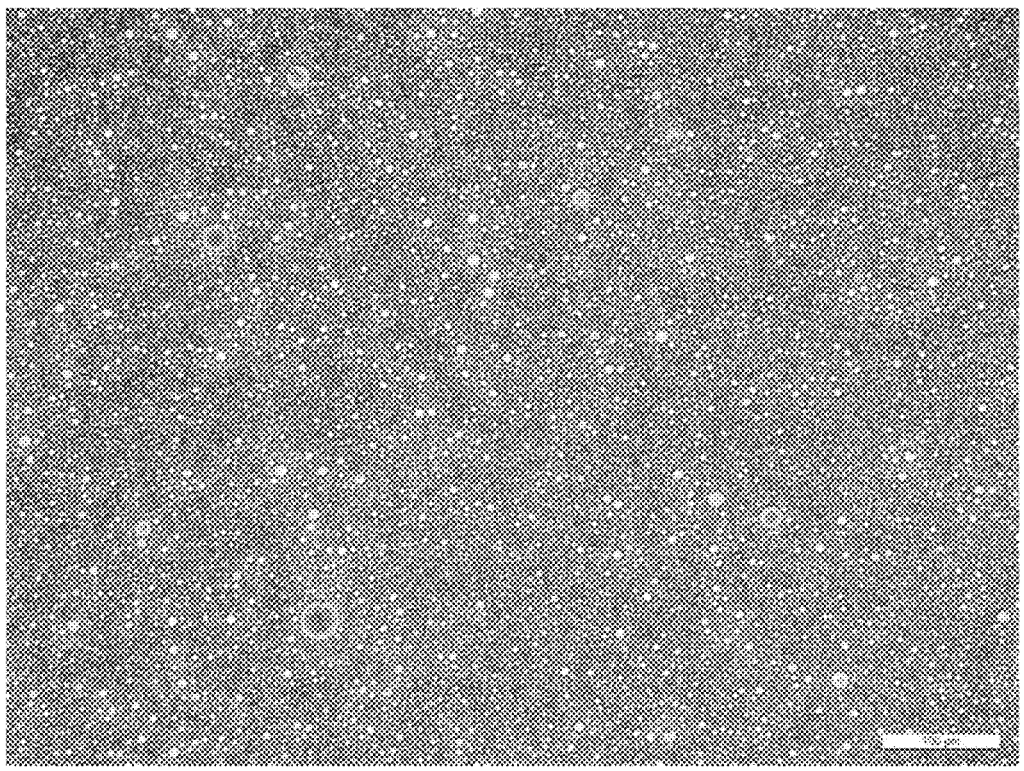
FIGS. 1 to 3 describe the present invention by way of example, without the invention—whose scope for application is apparent from the entire description and the claims—being restricted to the embodiments specified in the examples.

The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

The term "hyaluronic acid" or "HA" is used in the present invention to describe hyaluronic acid or a salt thereof if not expressly stated otherwise. The term "microbead" is used herein interchangeably with microdrop, microdroplet, microparticle, microsphere, nanobead, nanodrop, nanodroplet, nanoparticle, particle, nanosphere etc.

The content of hyaluronic acid may be determined according to the modified carbazole method (Bitter and Muir, 1962, *Anal Biochem.* 4: 330-334). Moreover, the number average molecular weight of the hyaluronic acid may be determined using standard methods in the art, such as those described by Ueno et al., 1988, *Chem. Pharm. Bull.* 36, 4971-4975; Wyatt, 1993, *Anal. Chim. Acta* 272: 1-40; and Wyatt Technologies, 1999, "Light Scattering University DAWN Course Manual" and "DAWN EOS Manual" Wyatt Technology Corporation, Santa Barbara, Calif.

Several aspects of the invention relate to various compositions and formulations comprising, among other constituents, an (effective) amount of the crosslinked HA product (the microbeads), and an active ingredient, preferably the active ingredient is a dermatological or cosmetic active agent; a personal care acceptable carrier, excipient or diluent, preferably a water-soluble excipient, and most preferably lactose.

In addition, aspects of the invention relate to articles comprising a product as defined in the first aspect or a composition as defined in the aspects and embodiments above, e.g., a cosmetic article, a sanitary article, or a personal care article in general. In a final aspect the invention relates to a cosmetic capsule or microcapsule comprising a product as defined in the first aspect or a composition as defined in other aspects and embodiments of the invention.

DETAILED DESCRIPTION OF THE INVENTION

The method of the invention to obtain crosslinked hyaluronic acid microbeads is now described in detail.

The method of producing crosslinked hyaluronic acid microbeads of the invention comprises the steps of:
(a) providing an aqueous alkaline solution comprising hyaluronic acid, or a salt thereof;
(b) forming microdroplets having a desired size from the mixed solution of step (a) in an organic or oil phase to form a water in organic or water in oil (W/O) emulsion, wherein the amount of oil phase used is of from 20 to less than 50% by weight based on the sum of oil phase and water;
(c) adding a solution comprising a crosslinking agent to the emulsion, whereby the reaction of hyaluronic acid with the crosslinking agent takes place to provide crosslinked hyaluronic acid microbeads; and
(d) optionally working up the dispersion of crosslinked hyaluronic acid microbeads.

Step (a):

The source of hyaluronic acid is not critical. Rooster combs have been a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP 0 694 616 discloses fermentation processes using an improved strain of *Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L., 1999, Cell. Mol. Life. Sci. 56: 670-682). WO 99/23227 discloses a Group I hyaluronate synthase from *Streptococcus equisimilis*. WO 99/51265 and WO 00/27437 describe a Group II hyaluronate synthase from *Pasturella multocida*. Ferretti et al. discloses the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (Proc. Natl. Acad. Sci. USA. 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as lyophilization or spray drying.

It can be advantageous when hyaluronic acid or salt thereof used is recombinantly produced, preferably by a Gram-positive bacterium or host cell, more preferably by a bacterium of the genus *Bacillus*. It has previously been described how to produce hyaluronic acid recombinantly in a *Bacillus* host cell, see WO 2003/054163, Novozymes A/S, which is incorporated herein in its entirety. Accordingly, in a preferred embodiment, the invention relates to the method of the first aspect, wherein the hyaluronic acid, or salt thereof, is recombinantly produced in a *Bacillus* host cell.

The host cell may be any *Bacillus* cell suitable for recombinant production of hyaluronic acid. The *Bacillus* host cell may be a wild-type *Bacillus* cell or a mutant thereof. *Bacillus* cells useful in the practice of the present invention include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. Mutant *Bacillus subtilis* cells particularly adapted for recombinant expression are described in WO 98/22598. Non-encapsulating *Bacillus* cells are particularly useful in the present invention.

In a preferred embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

The hyaluronic acid can be used itself or a salt of the hyaluronic acid can be used. It might be advantageous to use a salt, preferably an inorganic salt of hyaluronic acid. Preferred salts of hyaluronic acid useful in the present invention are sodium hyaluronate, potassium hyaluronate, ammonium hyaluronate, calcium hyaluronate, magnesium hyaluronate, zinc hyaluronate, or cobalt hyaluronate.

Various molecular weight fractions of hyaluronic acid have been described as advantageous for specific purposes. The hyaluronic acid, or salt thereof, used in the present invention has preferably a number average molecular weight of about 10,000 to about 10,000,000 Da, more preferably of from 25,000 to 5,000,000 Da and even more preferably of from 50,000 to 3,000,000 Da.

In a preferred embodiment of the invention, the hyaluronic acid or salt thereof has a number average molecular weight in the range of from 300,000 to 3,000,000 Da, preferably of from 400,000 to 2,500,000 Da, more preferably of from 500,000 to 2,000,000 Da, and most preferably in the range of from 500,000 to 1,000,000 Da.

In yet another preferred embodiment, the hyaluronic acid or salt thereof has a number average molecular weight in the range of between 10,000 and 300,000 Da, preferably in the range of from 20,000 to 200,000 Da, more preferably in the range of from 25,000 to 100,000 Da and most preferably in the range of from 25,000 to 80,000 Da.

The initial concentration of hyaluronic acid, or a salt thereof, in the aqueous alkaline solution of step a), might influence the properties of the resulting crosslinked microbeads. Therefore, a preferred embodiment of the invention relates to a method of the first aspect, wherein the aqueous alkaline solution comprises dissolved hyaluronic acid, or salt thereof, in a concentration of between 0.1%-40% (w/v), preferably of from 1 to 15% (w/v), and more preferably of from 4 to 6% (w/v).

The aqueous alkaline solution might be obtained by mixing the hyaluronic acid, or a salt thereof with an alkaline aqueous solution.

The aqueous alkaline solution might be prepared by adding a base, preferably an inorganic base, more preferably an alkali metal hydroxide and most preferably sodium hydroxide to water or a solution containing water. The pH value during the crosslinking reaction also influences the outcome. In a preferred embodiment of the invention the alkaline solution comprises dissolved alkal metal hydroxide, preferably sodium hydroxide in a concentration of from 0.001 to 2.0 M.

The solution of step (a) preferably has a pH of from 11 to 13, more preferably of from 11.5 to 12.5 and most preferably of about 12.

It might be advantageous to stir the solution of step (a) vigorously before using the solution in step (b).

Step (b):

For forming the emulsion in step (b) the amount of oil phase used is of from 20 to <50% by weight, preferably of from 25 to 45% by weight and more preferably of from 30 to 40% by weight based on the sum of oil phase and water.

It is preferred to use standard emollients used in cosmetic or personal care formulations as oil phase. Such standard emollients are not hydrocarbons or aromatic hydrocarbons, especially not toluene, o-xylene, dodecane, heptane, isooctane or cetylethylhexanoate. Preferred emollients used in the present invention are selected from mono- or diesters of linear and/or branched mono- and/or dicarboxylic acids having 2 to 44 C atoms with linear and/or branched saturated or unsaturated alcohols having 1 to 22 C atoms, the esterification products of aliphatic difunctional alcohols having 2 to 36 C atoms with monofunctional aliphatic carboxylic acids having 1 to 22 C atoms, long-chain aryl acid esters, such as e.g. esters of benzoic acid with linear and/or branched C6-C22-alcohols, or also benzoic acid isostearyl ester, benzoic acid butyloctyl ester or benzoic acid octyldodecyl ester, carbonates, preferably linear C6-C22-fatty alcohol carbonates, Guerbet carbonates, e.g. dicaprylyl carbonate, diethylhexyl carbonate, longer-chain triglycerides, i.e. triple esters of glycerol with three acid molecules, at least one of which is longer-chain, triglycerides based on C6-C10-fatty acids, linear or branched fatty alcohols, such as oleyl alcohol or octyldodecanol, and fatty alcohol ethers, such as dialykl ether e.g. dicaprylyl ether, silicone oils and waxes, e.g. polydimethylsiloxanes, cyclomethylsiloxanes, and aryl- or alkyl- or alkoxy-substituted polymethylsiloxanes or cyclomethylsiloxanes, Guerbet alcohols based on fatty alcohols having 6 to 18, preferably 8 to 10 carbon atoms, esters of linear C6-C22 fatty acids with linear C6-C22-fatty alcohols, esters of branched C6-C13-carboxylic acids with linear C6-C22-fatty alcohols, esters of linear C6-C22-fatty acids with branched C8-C18-alcohols, in particular 2-ethylhexanol or isononanol, esters of branched C6-C13-carboxylic acids with branched alcohols, in particular 2-ethylhexanol or isononanol, esters of linear and/or branched fatty acids with polyhydric alcohols (such as e.g. propylene glycol, dimer diol or trimer triol) and/or Guerbet alcohols, liquid mono-/di-/triglyceride mixtures based on C6-C18-fatty acids, esters of C6-C22-fatty alcohols and/or Guerbet alcohols with aromatic carboxylic acids, plant oils, branched primary alcohols, substituted cyclohexanes, ring-opening products of epoxidized fatty acid esters with polyols and/or silicone oils or a mixture of two or more of these compounds. The emollient used is preferably not miscible with water without phase separation.

Monoesters which are suitable as emollients and oil components are e.g. the methyl esters and isopropyl esters of fatty acids having 12 to 22 C atoms, such as e.g. methyl laurate, methyl stearate, methyl oleate, methyl erucate, isopropyl myristate, isopropyl palmitate, isopropyl stearate, isopropyl oleate. Other suitable monoesters are e.g. n-butyl stearate, n-hexyl laurate, n-decyl oleate, isooctyl stearate, isononyl palmitate, isononyl isononanoate, 2-ethylhexyl laurate, 2-ethylhexyl palmitate, 2-ethylhexyl stearate, 2-hexyldecyl stearate, 2-octyldodecyl palmitate, oleyl oleate, oleyl erucate, erucyl oleate and esters which are obtainable from technical-grade aliphatic alcohol cuts and technical-grade aliphatic carboxylic acid mixtures, e.g. esters of unsaturated fatty alcohols having 12 to 22 C atoms and saturated and unsaturated fatty acids having 12 to 22 C atoms, such as are accessible from animal and plant fats. However, naturally occurring monoester and wax ester mixtures such as are present e.g. in jojoba oil or in sperm oil are also suitable. Suitable dicarboxylic acid esters are e.g. di-n-butyl adipate, di-n-butyl sebacate, di-(2-ethylhexyl) adipate, di-(2-hexyldecyl) succinate, di-isotridecyl azelate. Suitable diol esters are e.g. ethylene glycol dioleate, ethylene glycol di-isotridecanoate, propylene glycol di-(2-ethylhexanoate), butanediol di-isostearate, butanediol di-caprylate/caprate and neopentyl glycol di-caprylate.

There may be mentioned here by way of example fatty acid triglycerides; as such, for example, natural plant oils, e.g. olive oil, sunflower oil, soya oil, groundnut oil, rapeseed oil, almond oil, sesame oil, avocado oil, castor oil, cacao butter, palm oil, but also the liquid contents of coconut oil or of palm kernel oil, as well as animal oils, such as e.g. shark-fish liver oil, cod liver oil, whale oil, beef tallow and butter-fat, waxes, such as beeswax, carnauba palm wax, spermaceti, lanolin and neat's foot oil, the liquid contents of beef tallow or also synthetic triglycerides of caprylic/capric acid mixtures, triglycerides from technical-grade oleic acid, triglycerides with isostearic acid, or from palmitic acid/oleic acid mixtures, can be employed as emollients (oil phase).

The preferred emollients useful as oil phase in the present invention are diethylhexyl carbonate or decyl cocoate or mixtures thereof.

By using said emollients as oil phase it is not necessary to remove the oil phase from the microbeads dispersion when the emollient is useful for formulating a cosmetic or personal care composition.

It might be helpful to add one or more emulsifier in step (a) or Step (b) to prepare the emulsion. Emulsifier useful in the present invention can be selected from those, listed below as additional components.

It might by advantageous when the microdroplets formed in step (b) have a number average diameter in the range of from about 1 nanometre to 1 millimetre. The maximum of the particle size distribution of the microdroplets of step (b) is preferably in the range of from 0.1 to 100 µm, more preferably from 0.5 to 10 µm and most preferably from 1 to 2 µm. The size of the droplets can be adjusted by the choice of emulsifier used and the intensity of stirring. The combination of emulsifier used and intensity of stirring necessary to obtain droplets with the desired size can be determined by simple test series. The size of the droplets or microbeads can be determined with an Accusizer (Accusizer 780 Optical Particle Sizer, PSS NICOMP, Santa Barbara, Calif., USA with Accusizer 780AD CW788-Nicomp software, V1.68 (2000)).

Preferred emulsifiers used in the present invention are selected from those having a HLB-value of from 3 to 9, preferably 4 to 6 and more preferably about 5. Preferred emulsifiers are selected from polyglyceryl-4-diisostearat/polyhydroxysterat/sebacat (ISOLAN® GPS), PEG/PPG-10/1 dimethicone, (ABIL® EM 90), Polyglyceryl-4 Isostearate (ISOLAN® GI 34), Polyglyceryl-3 Oleate (ISOLAN® GO 33), Methylglucose Isostearate (ISOLAN® IS), Diisostearoyl Polyglyceryl-3 Dimer Dilinoleate (ISOLAN® PDI), Glyceryl Oleate (TEGIN® 0 V), Sorbitan Laurate (TEGO® SML), Sorbitan Oleate (TEGO® SMO V) and Sorbitan Stearate (TEGO® SMS). These preferred emulsifiers are available from Evonik Goldschmidt GmbH.

Step (c):

The concentration of the crosslinking agent might have a profound impact on the resulting microbeads. Consequently, a preferred embodiment of the invention relates to a method of the first aspect, wherein the crosslinking agent (CA) in a weight ratio of between 1:1 and 100:1 of hyaluronic acid or a salt thereof (HA)/crosslinking agent (CA) (dry weight), preferably between 2:1 and 50:1 of HA/CA (dry weight).

The degree of crosslinking is preferably in the range of from 0.001 to 1, more preferably of from 0.01 to 0.5 and even more preferably about 0.1. A degree of crosslinking of 1 means that one mol of a n-functional OH-reactive compound is reacted with n mol monosaccharide of the hyaluronic acid. The degree of crosslinking can be determined by analyzing the amount of non reacted crosslinker in the reaction mixture. The analytic can be done by known analytical methods, e.g. HPLC.

Crosslinking agents suitable for the methods of the instant invention are for example poly functional (>=2) OH-reactive compounds. Examples for suitable crosslinking agents are divinylsulfone (DVS) or crosslinking agents based on bisepoxide crosslinking technology, for example GDE=glycerol diglycidyl ether or BDE: 1,4-butanediyl diglycidyl ether. The crosslinking agent is preferably selected from divinylsulfone, glycerol diglycidyl ether or 1,4-butanediyl diglycidyl ether. The most preferred crosslinking agent of the invention is divinylsulfone which is preferably used in the weight ratio mentioned above.

The crosslinking might be added directly or as a solution. If the crosslinking agent is added as a solution the crosslinking agent is preferably solved in an oil phase, preferably the same oil phase as used in step (b). It might be advantageous to add the crosslinking agent as a solution which comprises a $C_1$ to $C_4$-alcohol, preferably ethanol. It might be more advantageous to add the crosslinking agent as a solution which comprises an oil phase as mentioned above and a $C_1$- to $C_4$-alcohol, preferably ethanol. Using a crosslinking agent solution comprising ethanol might result in a faster distribution of the crosslinking agent into the micro droplets. Preferred solutions of crosslinking agents comprise a mixture of from 20 to 80% by weight, preferably 40 to 60% by weight of the oil phase and from 80 to 20% by weight, preferably 40 to 60% by weight of $C_1$- to $C_4$-alcohol as solvent.

The inventors found that an initial period of stirring during and/or immediately after mixing the solution comprising the crosslinking agent and the HA-solution in step (c) was desirable to achieve satisfactory gelling. Accordingly the addition of the solution comprising the crosslinking agent is done under stirring, preferably vigorous stirring. It might be advantageous to add the solution comprising the crosslinking agent in step (c) in a period of time of from 1 to 180 minutes, preferably while stirring. It might be preferred, to stir for another period of time of from 1 to 180 minutes after adding the last amount of solution comprising the crosslinking agent.

The reaction of hyaluronic acid or the salt thereof with the crosslinking agent, preferably the divinylsulfone takes preferably place at a temperature of from 0° C. to 100° C., more preferably of from 10° C. to 50° C., and even more preferably of from 20° C. to 30° C.

The present inventors determined that a heating step was beneficial after mixing the solutions. Accordingly, a preferred embodiment of the invention relates to a method of the first aspect, wherein the mixed solution of step (c) is heated to a temperature in the range of 20° C.-100° C., preferably in the range of 25° C.-80° C., more preferably in the range of 30° C.-60° C., and most preferably in the range of 35° C.-55° C., and wherein the temperature is maintained in this range for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes after mixing the solutions; preferably without stirring.

In another preferred embodiment of the invention it is advantageous to leave the reaction mixture of step (c) at room temperature for a brief period after the crosslinking reaction has taken place, but still with continuous stirring.

In a preferred embodiment of the method of the invention, the reaction mixture of step (c) is maintained after the reaction has taken place for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes, at a temperature in the range of 0° C.-40° C., preferably in the range of 10° C.-30° C.

The crosslinked microbeads resulting from step (c) have preferably a number average diameter in the range of from about 1 nanometer to 1 millimeter. The maximum of the particle size distribution of the crosslinked microbreads of step (c) of the invention is preferably in the range of from 0.1 to 100 µm, more preferably from 0.5 to 10 µm and most preferably from 1 to 2 µm.

It might be advantageous to obtain a dispersion in step (c) that comprises almost none unreacted crosslinking agent. Preferably the dispersion more preferably the microbeads comprise less than 10 ppm by weight (wppm), more preferably less than 5 wppm. The concentration of free crosslinking agent in the dispersion especially needs to be low if the dispersion is directly used for formulating cosmetic or personal care compositions because the unreacted crosslinking agent might be a toxicological threat. It is therefore preferred to last the reaction of step (c) till a dispersion is obtained comprising the unreacted crosslinking agent in the concentration mentioned above.

Optional Step (d)

The optional step d) can for example be a neutralization and/or a separation step.

For neutralization, the crosslinked microbeads directly or after a separation form the dispersion might be contacted at least once with water, water and an acid, water and a buffer, especially water and a phosphate buffer, water and a saline buffer, or water and a phosphate buffer and a saline buffer. Preferably the optional step (d) comprises neutralizing the pH of the crosslinked microbeads with a buffer or an acid. Many types of buffers or acids, as are well known to the skilled person, have been envisioned as suitable for the swelling and neutralizing of the crosslinked microbeads in step d) of the invention. The acids or acid solutions used are preferably selected from the group comprising fatty acids liquid at 25° C., especially lactic acid, oleic acid or isostearic acid. It might be advantageous to use aqueous solutions of acids comprising of from 75 to 95% by weight, preferably from 80 to 90% by weight of water soluble acid, e.g. lactic acid. Preferably the crosslinked microbeads are contacted with a liquid, especially an aqueous acid solution or an aqueous buffer with a pH value in the range of from 2.0 to 10.0, preferably in the range of from 5.0 to 9.5. If the neutralization is done without separation of the microbeads it is advantageous not to use mineral acids for neutralization because such acids might result in the destruction of the emulsion/dispersion.

A preferred suitable buffer is chosen with a pH value, which results in that the crosslinked microbeads have a pH value of from 7 to 9.5, preferably of from 8.5 to 9.5 and more preferably of about 9. It is estimated that the pH of the dispersion (the liquid comprising the microbeads) is essentially the same as the pH value of the microbeads. The pH of the microbeads can therefore be easily determined by well known methods, e.g. putting pH paper or a pH electrode of a pH meter into the dispersion.

It is preferred that the buffer in the method of the first aspect comprises a phosphate buffer and/or a saline buffer.

An optional purifying step may comprise any separation technique known in the art, e.g. filtration, decantation, centrifugation and so on. Preferably the optional step (d) is a purifying step which comprises dialyzing the crosslinked microbeads against de-ionized water using a dialysis membrane that allows free diffusion of molecules having a size less than 13,000 Daltons.

It might be advantageous to combine one or more purifying steps with one or more neutralizing steps.

When using emollients as oil phase that are acceptable emollients for personal care formulation a separation or purifying step might not be necessary. The dispersion obtained from step (c) might directly or after a neutralization be used to formulate a cosmetic or personal care composition.

With the method of the invention the microbeads of the invention might be obtained. Preferred microbeads of the invention comprise hyaluronic acid, or a salt thereof, crosslinked with divinylsulfone. This preferred microbead of the invention might as well be obtained by the method of the invention.

A preferred microbead of the invention is approximately spherical. The microbeads of the invention preferably have a maximum of the distribution of the cross-section or diameter in the range of between 1 nanometer to 1 millimeter, more preferably of from 0.01 to 1000 µm, even more preferably of from 0.1 to 100 µm and most preferably of from 0.5 to 10 µm. Though, usually the microbeads of the present invention will be made with a desired size in a much more narrow range, i.e., they will be fairly uniform. The crosslinked microbeads resulting from step (c) have preferably a number average diameter in the range of from about 1 nanometer to 1 millimeter. The microbeads preferably have a number average diameter in the range of about 100 to 1,000 nanometer; or in the range of more than 1,000 nanometer to 1,000 micrometer. The polydispersity of the microbeads of the invention is preferably narrow, which means that more than 95%, preferably more than 97% of the particles are smaller or equal to the tenfold of the maximum of the particle size distribution. The polydispersity can be determined by single particle optical sizing with the Accusizer method mentioned above.

Preferred microbeads of the invention are obtained using hyaluronic acids or salt thereof with a number average molecular weight of about 10,000 to about 10,000,000 Da, more preferably of from 25,000 to 5,000,000 Da and even more preferably of from 50,000 to 3,000,000 Da.

In a preferred embodiment of the invention, the microbeads are obtained using hyaluronic acid or salt thereof having a number average molecular weight in the range of from 300,000 to 3,000,000 Da, preferably of from 400,000 to 2,500,000 Da, more preferably of from 500,000 to 2,000,000 Da, and most preferably in the range of from 500,000 to 1,000,000 Da.

In yet another preferred embodiment, the microbeads are obtained using hyaluronic acid or salt thereof having a number average molecular weight in the range of between 10,000 and 300,000 Da, preferably in the range of from 20,000 to 200,000 Da, more preferably in the range of from 25,000 to 100,000 Da and most preferably in the range of from 25,000 to 80,000 Da.

Preferred microbeads comprise as inorganic salt of the hyaluronic acid, sodium hyaluronate, potassium hyaluronate, ammonium hyaluronate, calcium hyaluronate, magnesium hyaluronate, zinc hyaluronate, or cobalt hyaluronate.

The microbead of the invention might comprise an active ingredient, a water-soluble excipient, and/or a preservative, or other ingredients. Preferably the active ingredient is a personal care active substance. The microbeads of the invention may comprise at least one additional component chosen from the group of emollients, emulsifiers and surfactants, thickeners/viscosity regulators/stabilizers, UV light protection filters, antioxidants, hydrotropic agents (or polyols), solids and fillers, film-forming agents, pearlescent additives, deodorant and antiperspirant active compounds, insect repellents, self-tanning agents, preservatives, conditioning agents, perfumes, dyestuffs, biogenic active compounds, care additives, super-oiling agents, moisturizers and solvents in their inside.

The microbeads of the invention give access to the compositions of the invention comprising these microbeads. The compositions of the invention may comprise at least one additional component chosen from the group of emollients, emulsifiers and surfactants, thickeners/viscosity regulators/stabilizers, UV light protection filters, antioxidants, hydrotropic agents (or polyols), solids and fillers, film-forming agents, pearlescent additives, deodorant and antiperspirant active compounds, insect repellents, self-tanning agents, preservatives, conditioning agents, perfumes, dyestuffs, biogenic active compounds, care additives, super-oiling agents, moisturizers and solvents. The additional components might be inside and/or outside the microbeads. Preferably the additional ingredients are present in the composition of the invention outside the microbeads only.

As mentioned above it might be advantageous if the products of the invention, e.g. the microbeads or compositions or dispersions comprising those microbeads also comprise other ingredients (additional components). The other ingredients might be inside the microbeads or inside and/or outside of the microbeads if the product of the invention is a composition or dispersion. Other ingredients that might be useful are preferably one or more active ingredient, preferably one or more personal care active substance, especially biogenic actives, and/or one or more water-soluble excipient.

A water-soluble excipient may be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Preferred examples of additional component chosen from the group of emollients, emulsifiers and surfactants, thickeners/viscosity regulators/stabilizers, UV light protection filters, antioxidants, hydrotropic agents (or polyols), solids and fillers, film-forming agents, pearlescent additives, deodorant and antiperspirant active compounds, insect repellents, self-tanning agents, preservatives, conditioning agents, perfumes, dyestuffs, biogenic active compounds, care additives, superoiling agents and solvents are given below.

Emulsifiers or surfactants which can be employed as additional components are nonionic, anionic, cationic or amphoteric surfactants.

Compounds from at least one of the following groups can be employed as nonionic emulsifiers or surfactants: addition products of from 2 to 100 mol of ethylene oxide and/or 0 to 5 mol of propylene oxide on linear fatty alcohols having 8 to 22 C atoms, on fatty acids having 12 to 22 C atoms and on alkylphenols having 8 to 15 C atoms in the alkyl group, C12/18-fatty acid mono- and diesters of addition products of from 1 to 100 mol of ethylene oxide on glycerol, glycerol mono- and diesters and sorbitan mono- and diesters of saturated and unsaturated fatty acids having 6 to 22 carbon atoms and ethylene oxide addition products thereof, alkyl mono- and oligoglycosides having 8 to 22 carbon atoms in the alkyl radical and ethylene oxide addition products thereof, addition products of from 2 to 200 mol of ethylene oxide on castor oil and/or hydrogenated castor oil, partial esters based on linear, branched, unsaturated or saturated C6-C22-fatty acids, ricinoleic acid and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), mono-, di- and trialkyl phosphates and mono-, di- and/or tri-PEG-alkyl phosphates and salts thereof, polysiloxane/polyether copolymers (Dimethicone Copolyols), such as e.g. PEG/PPG-20/6 Dimethicone, PEG/PPG-20/20 Dimethicone, Bis-PEG/PPG-20/20 Dimethicone, PEG-12 or PEG-14 Dimethicone, PEG/PPG-14/4 or 4/12 or 20/20 or 18/18 or 17/18 or 15/15, polysiloxane/polyalkyl polyether copolymers and corresponding derivatives, such as e.g. Lauryl or Cetyl Dimethicone Copolyols, in particular Cetyl PEG/PPG-10/1 Dimethicone (ABIL® EM 90 (Evonik Degussa)), mixed esters of pentaerythritol, fatty acids, citric acid and fatty alcohol according to DE 11 65 574 and/or mixed esters of fatty acids having 6 to 22 carbon atoms, methylglucose and polyols, such as e.g. glycerol or polyglycerol, citric acid esters, such as e.g. Glyceryl Stearate Citrate, Glyceryl Oleate Citrate and Dilauryl Citrate.

Anionic emulsifiers or surfactants can contain groups which confer solubility in water, such as e.g. a carboxylate, sulphate, sulphonate or phosphate group and a lipophilic radical. Anionic surfactants which are tolerated by skin are known in large numbers to the person skilled in the art and are commercially obtainable. In this context these can be alkyl sulphates or alkyl phosphates in the form of their alkali metal, ammonium or alkanolammonium salts, alkyl ether-sulphates, alkyl ether-carboxylates, acyl sarcosinates and sulphosuccinates and acyl glutamates in the form of their alkali metal or ammonium salts.

Cationic emulsifiers and surfactants can also be added. Quaternary ammonium compounds, in particular those provided with at least one linear and/or branched, saturated or unsaturated alkyl chain having 8 to 22 C atoms, can be employed in particular as such, thus, for example, alkyltrimethylammonium halides, such as e.g. cetyltrimethylammonium chloride or bromide or behenyltrimethylammonium chloride, but also dialkyldimethylammonium halides, such as e.g. distearyldimethylammonium chloride.

Monoalkylamidoquats, such as e.g. palmitamidopropyltrimethylammonium chloride, or corresponding dialkylamidoquats can furthermore be employed.

Readily biodegradable quaternary ester compounds, which can be quaternized fatty acid esters based on mono-, di- or triethanolamine, can furthermore be employed. Alkylguanidinium salts can furthermore be admixed as cationic emulsifiers.

Typical examples of mild surfactants, i.e. surfactants which are particularly tolerated by skin, are fatty alcohol polyglycol ether-sulphates, monoglyceride sulphates, mono- and/or dialkyl sulphosuccinates, fatty acid isethionates, fatty acid sarcosinates, fatty acid taurides, fatty acid glutamates, ether-carboxylic acids, alkyl oligoglucosides, fatty acid glucamides, alkylamidobetaines and/or protein-fatty acid condensates, the latter for example based on wheat proteins.

It is furthermore possible to employ amphoteric surfactants, such as e.g. betaines, amphoacetates or amphopropionates, thus e.g. substances such as the N-alkyl-N,N-dimethylammonium glycinates, for example coco-alkyldimethylammonium glycinate, N-acylaminopropyl-N,N-dimethylammonium glycinates, for example coco-acylamimopropyldimethylammonium glycinate, and 2-alkyl-3-carboxymethyl-3-hydroxyethylimidazolines having in each case 8 to 18 C atoms in the alkyl or acyl group, and coco-acylaminoethylhydroxyethylcarboxymethyl glycinate.

Of the ampholytic surfactants, those surface-active compounds which contain, apart from a C8/18-alkyl or -acyl group, at least one free amino group and at least one —COOH or —SO3H group in the molecule and are capable of formation of inner salts can be employed. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 C atoms in the alkyl group. Further examples of ampholytic surfactants are N-coco-alkylaminopropionate, coco-acylaminoethylaminopropionate and C12/18-acrylsarcosine.

Preferred emulsifiers or surfactants used for formulating the composition are identical to those used in the production of the microbeads.

Suitable thickeners are, for example, polysaccharides, in particular xanthan gum, guar-guar, agar-agar, alginates and tyloses, carboxymethylcellulose and hydroxyethylcellulose, furthermore higher molecular weight polyethylene glycol mono- and diesters of fatty acids, polyacrylates (e.g. Carbopols TM or Synthalens TM), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with a restricted distribution of homologues or alkyl oligoglucosides, and electrolytes, such as sodium chloride and ammonium chloride.

Possible thickeners for thickening oily phases are all the thickening agents known to the person skilled in the art. In this context there may be mentioned in particular waxes, such as hydrogenated castor wax, beeswax or microwax. Inorganic thickening agents can furthermore also be employed, such as silica, alumina or laminar silicates (e.g. hectorite, laponite, saponite). In this context, these inorganic thickeners for the oily phase can be hydrophobically modified. In this context, Aerosils, laminar silicates and/or metal salts of fatty acids, such as e.g. zinc stearate, can be employed in particular for thickening/stabilizing water-in-oil emulsions.

The formulations can comprise as viscosity regulators for aqueous surfactant systems e.g. NaCl, low molecular weight nonionic surfactants, such as Cocoamide DEA/MEA and Laureth-3, or polymeric, high molecular weight, associative, highly ethoxylated fat derivatives, such as PEG-200 Hydrogenated Glyceryl Palmate.

UV light protection filters which can be employed are, for example, organic substances which are capable of absorbing ultraviolet rays and of releasing the energy absorbed again in the form of longer-wavelength radiation, e.g. heat. UVB filters can be oil-soluble or water-soluble. Oil-soluble UVB light protection filters which may be mentioned are e.g.: 3-benzylidenecamphor and derivatives thereof, e.g. 3-(4-methylbenzylidene)camphor (INCI: 4-Methylbenzylidene Camphor, trade name: Eusolex 6300), 4-aminobenzoic acid derivatives, such as e.g. 4-(dimethylamino)-benzoic acid 2-ethylhexyl ester, 4-(dimethylamino)benzoic acid 2-ethylhexyl ester and 4-(dimethylamino)benzoic acid amyl ester, ester of cinnamic acid, such as e.g. 4-methoxycinnamic acid 2-ethylhexyl ester (INCI: Octyl Methoxycinnamate, trade name: Parsol® MCX), 4-methoxycinnamic acid isopentyl ester, 2-ethylhexyl 2-cyano-3,3-diphenylacrylate (INCI: Octocrylene; trade name: Uvinul N-539), esters of salicylic acid, such as e.g. salicylic acid 2-ethylhexyl ester, salicylic acid 4-isopropylbenzyl ester, salicylic acid homomethyl ester, derivatives of benzophenone, such as e.g. 2-hydroxy-4 methoxybenzophenone, 2-hydroxy-4-methoxy-4'-methylbenzophenone, 2,2'-dihydroxy-4-methoxybenzophenone, 2-(4'-diethylamino-2'-hydroxybenzoyl)-benzoic acid hexyl ester (also: aminobenzophenone), esters of benzalmalonic acid, such as e.g. 4-methoxybenzmalonic acid di-2-ethylhexyl ester, triazine derivatives, such as e.g. 4,4',4"-(1,3,5-triazine-2,4,6-triylriimino)-tris-benzoic acid tris(2-ethylhexyl ester) (also: 2,4,6-tris-[anilino-(p-carbo-2'-ethyl-1'-hexyloxy)]-1,3,5-triazine, INCI: Octyl Triazone, marketed by BASF Aktiengesellschaft under the trade name UVINUL® T 150), 2,4-bis-{[4-(2-ethyl-hexyloxy)-2-hydroxy]-phenyl}-6-(4-methoxyphenyl)-1,3,5-triazine (INCI: Aniso Triazine, obtainable under the trade name Tinosorb® S), dioctylbutylamidotriazone (INCI: Dioctylbutamidotriazone), 2,4-bis-[5-1(dimethylpropyl)benzoxazol-2-yl-(4-phenyl)-imino]-6-(2-ethylhexyl)-imino-1,3,5-triazine with the CAS no. 288254-16-0, obtainable from 3V Sigma under the trade name Uvasorb® K2A), 2,4-bis-{[4-(2-ethyl-hexyloxy)-2-hydroxy]-phenyl}-6-(4-methoxyphenyl)-1,3,5-triazine (INCI: Bis-ethylhexyloxyphenol Methoxyphenyl Triazine), obtainable under the trade name Tinosorb® S from CIBA-Chemikalien GmbH and 2-[4,6-bis (2,4-dimethylphenyl)-1,3,5-triazin-2-yl]-5-(octyloxy)phenol (CAS no.: 2725-22-6), propane-1,3-diones, such as e.g. 1-(4-tert-butylphenyl)-3-(4'-methoxyphenyl)propane-1,3-dione.

UV-B filters which are particularly preferably employed here are the UV light protection filter substances 2-cyano-3-phenyl-cinnamic acid 2-ethylhexyl ester, 2,4-bis-{[4-(2-ethyl-hexyloxy)-2-hydroxy]-phenyl}-6-(4-methoxyphenyl)-1,3,5-triazine, dioctylbutylamidotriazone, 2-hydroxy-4-methoxybenzophenone, 2-hydroxy-4-methoxy-4'-methylbenzophenone, 2,2'-dihydroxy-4-methoxybenzophenone, 4-methoxybenzmalonic acid di-2-ethylhexyl ester, 2,4,6-tris-[anilino-(p-carbo-2'-ethyl-1'-hexyloxy)]-1,3,5-triazine, 2,4-bis-[5-1(dimethylpropyl) benzoxazol-2-yl-(4-phenyl)-imino]-6-(2-ethylhexyl)-imino-1,3,5-triazine, 2,4-Bis-{[4-(2-ethyl-hexyloxy)-2-hydroxy]-phenyl}-6-(4-methoxyphenyl)-1,3,5-triazine and 2-[4,6-Bis (2,4-dimethylphenyl)-1,3,5-triazin-2-yl]-5-(octyloxy) phenol.

UV-A filters which are preferably employed are 1-(4'-tert-butylphenyl)-3-(4'-methoxyphenyl)-propane-1,3-dione, 1-phenyl-3-(4'-isopropylphenyl)propane-1,3-dione.

Particularly preferred UV-A filters are 4-(tert-butyl)-4'-methoxydibenzoylmethane (CAS no. 70356-09-1), which is sold by Givaudan under the trademark Parsol® 1789 and by Merck under the trade name Eusolex® 9020, and hydroxybenzophenones according to DE 102004027475, particularly preferably 2-(4'-diethylamino-2'-hydroxybenzoyl)-benzoic acid hexyl ester (also: aminobenzophenone), which is obtainable under the name Uvinul A Plus from BASF.

UV filter substances which are moreover preferred are furthermore so-called broad-band filters, i.e. filter substances which absorb both UV-A and UV-B radiation. Within this group, 2,2'-methylene-bis-(6-(2H-benzotriazol-2-yl)-4-(1,1,3,3-tetramethylbutyl)-phenol, which is obtainable under the trade name Tinosorb® M from CIBA-Chemikalien GmbH, and 2-(2H-benzotriazol-2-yl)-4-methyl-6-[2-methyl-3-[1,3,3,3-tetramethyl-1-[(trimethylsilyl)oxy]-disiloxanyl]propyl]-phenol (CAS no.: 155633-54-8) with the INCI name Drometrizole Trisiloxane, are preferably employed.

The use of a combination of several different UV filters is preferred.

In addition to the soluble substances mentioned, insoluble pigments, namely finely disperse metal oxides and salts, are also possible for this purpose, such as, for example, titanium dioxide, zinc oxide, iron oxide, aluminium oxide, cerium oxide, zirconium oxide, silicates (talc), barium sulphate and zinc stearate. In this context, the particles should have an average diameter of less than 100 nm, e.g. between 5 and 50 nm and in particular between 15 and 30 nm. They can have a spherical shape, but those particles which have an ellipsoid shape or a shape which deviates otherwise from the spherical can also be employed.

Micronized organic pigments, such as, for example, 2,2'-methylene-bis-{6-(2H-benzotriazole-2-yl)-4-(1,1,3,3-tetramethylbutyl)phenol} having a particle size of <200 nm, which is obtainable e.g. as a 50% strength aqueous dispersion, are a relatively novel class of light protection filters.

Further suitable UV light protection filters are moreover to be found in the overview by P. Finkel in SÖFW-Journal 122, 543 (1996).

The amount of UV light protection filters employed is preferably 0.01-15%, preferably 0.05-10%, particularly preferably 0.1-5%, based on the formulation.

In addition to the two abovementioned groups of primary UV light protection filters, secondary light protection agents of the antioxidant type which interrupt the photochemical reaction chain triggered when UV radiation penetrates into the skin can also be employed. Antioxidants which can be employed are e.g. superoxide dismutase, tocopherols (vitamin E), dibutylhydroxytoluene and ascorbic acid (vitamin C).

Hydrotropic agents which can be employed for improving the flow properties and the use properties are, for example, ethanol, isopropyl alcohol or polyols. Polyols which are possible here can have 2 to 15 carbon atoms and at least two hydroxyl groups. Typical examples are: glycerol, alkylene glycols, such as, for example, ethylene glycol, diethylene glycol, propylene glycol, butylene glycol, hexylene glycol and polyethylene glycols having an average molecular weight of from 100 to 1,000 Dalton, technical-grade oligoglycerol mixtures having a degree of self-condensation of from 1.5 to 10, such as, for example, technical-grade diglycerol mixtures having a diglycerol content of from 40 to 50 wt. %, methylol compounds, such as, in particular, trimethylolethane, trimethylolpropane, trimethylolbutane, pentaerythritol and dipentaerythritol, lower alkyl glucosides, in particular those having 1 to 4 carbon atoms in the alkyl radical, such as, for example, methyl and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine.

Solids which can be employed are, for example, iron oxide pigments, titanium dioxide or zinc oxide particles and those additionally mentioned under "UV stabilizers". Particles which lead to specific sensorial effects can furthermore also be employed, such as, for example, nylon 12, boron nitride, polymer particles, such as, for example, polyacrylate or polymethacrylate particles, or silicone elastomers. Fillers which can be employed include starch and starch derivatives, such as tapioca starch, distarch phosphate, aluminium- or sodium-starch, octenyl succinate and pigments which have neither a chiefly UV filter nor a colouring action, for example Aerosile® (CAS no. 7631-86-9).

Film-forming agents, e.g. for improving the water resistance, which can be employed are, for example: polyurethanes, Dimethicone Copolyol, polyacrylates or PVP/VA copolymer (PVP=polyvinylpyrrolidone, VA=vinyl acetate). Fat-soluble film-forming agents which can be employed are: e.g. polymers based on polyvinylpyrrolidone (PVP), copolymers of polyvinylpyrrolidone, PVP/hexadecene copolymer or PVP/eicosene copolymer.

Pearlescent additives which can be employed are e.g. glycol distearates or PEG-3 Distearate.

Possible deodorant active compounds are e.g. odour maskers, such as the usual perfume constituents, odour absorbers, for example the laminar silicates described in the patent laid-open specification DE 40 09 347, and of these in particular montmorillonite, kaolinite, ilite, beidelite, nontronite, saponite, hectorite, bentonite, smectite, furthermore, for example, zinc salts of ricinoleic acid. Germ-inhibiting substances are likewise suitable for incorporation. Germ-inhibiting substances are, for example, 2,4,4'-trichloro-2'-hydroxydiphenyl ether (Irgasan), 1,6-di-(4 chlorophenylbiguanido)-hexane (chlorhexidine), 3,4,4' trichlorocarbanilide, quaternary ammonium compounds, clove oil, mint oil, thyme oil, triethyl citrate, farnesol, (3,7,11-trimethyl-2,6,10-dodecatrien-1-ol), ethylhexyl glyceryl ether, poly-glyceryl-3 caprylate (TEGO® Cosmo P813, Evonik Degussa), and the active agents described in the patent laid-open specifications DE 198 55 934, DE 37 40 186, DE 39 38 140, DE 42 04 321, DE 42 29 707, DE 42 29 737, DE 42 38 081, DE 43 09 372, DE 43 24 219 and EP 0 666 732.

Antiperspirant active compounds which can be employed are astringents, for example basic aluminium chlorides, such as aluminium chlorohydrate ("ACH") and aluminium zirconium glycine salts ("ZAG").

Insect repellents which can be employed are, for example, N,N-diethyl-m-toluamide, 1,2-pentanediol, or Insect Repellent 3535.

Self-tanning agents which can be employed are e.g. dihydroxyacetone and erythrulose.

Preservatives which can be employed are, for example, mixtures of individual or several alkylparaben esters with phenoxyethanol. The alkylparaben esters can be methylparaben, ethylparaben, propylparaben and/or butylparaben. Instead of phenoxyethanol, other alcohols, such as, for example, benzyl alcohol or ethanol, can also be employed. Other conventional preservatives can moreover also be employed, such as, for example, sorbic or benzoic acid, salicylic acid, 2-bromo-2-nitropropane-1,3-diol, chloroacetamide, Diazolidinyl Urea, DMDM Hydantoin, Iodopropynyl Butyl Carbamate, Sodium Hydroxymethylglycinate, methylisothiazoline, chloromethyl-isothiazoline, ethylhexylglycerol or Caprylyl Glycol.

Conditioning agents which can be used are e.g. organic quaternary compounds, such as cetrimonium chloride, dicetyldimonium chloride, behenyltrimonium chloride, distearyldimonium chloride, behenyltrimonium methosulphate, distearoylethyldimonium chloride, palmitamidopropyltrimonium chloride, Guar Hydroxypropyltrimonium Chloride, Hydroxypropyl-guar, Hydroxypropyltrimonium Chloride or Quaternium-80, or also amine derivatives, such as e.g. aminopropyldimethicone or stearamidopropyldimethylamine.

Perfumes which can be employed are natural or synthetic odoriferous substance or mixtures thereof. Natural odoriferous substances are extracts from blossom (lily, lavender, rose, jasmine, orange-blossom, ylang-ylang), stems and leaves (geranium, patchouli, petitgrain), fruit (aniseed, coriander, caraway, juniper), fruit peel (bergamot, lemon, orange), roots (mace, angelica, celery, cardamom, costus, iris, thyme), needles and branches (spruce, fir, pine, dwarf pine), resins and balsams (galbanum, elemi, benzoin, myrrh, frankincense, opoponax). Animal raw materials are furthermore possible, such as, for example, civet and castoreum. Typical synthetic odoriferous compounds are products of the ester, ether, aldehyde, ketone, alcohol and hydrocarbon type. Odoriferous compounds of the ester types are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethyl-phenylglycinate, allyl cyclohexylpropionate, styrallyl propionate and benzyl salicylate. The ethers include, for example, benzyl ethyl ether, the aldehydes include e.g. the linear alkanals having 8 to 18 carbon atoms, citral, citronellal, citronellyloxy-acetaldehyde, cyclamen aldehyde, hydroxycitronellal, lilial and bourgeonal, the ketones include e.g. the ionones, α-isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. Mixtures of various odoriferous substances which together generate a pleasant fragrance note can be employed. Essential oils of low volatility, which are usually employed as aroma components, are also suitable as perfumes, e.g. sage oil, chamomile oil, clove oil, Melissa oil, mint oil, cinnamon leaf oil, linden blossom oil, juniper berry oil, vetiver oil, frankincense oil, galbanum oil, labolanum oil and lavandin oil. Bergamot oil, dihydromyrcenol, lilial, lyral, citronellol, phenylethyl alcohol, α-hexylcinnamaldehyde, geraniol, benzylacetone, cyclamen aldehyde, linalool, Boisambrene Forte, ambroxan, indole, hedione, sandelice, lemon oil, mandarin oil, orange oil, allyl amylglycollate, cyclovertal, lavandin oil, clary sage oil, β-damascone, Bourbon geranium oil, cyclohexyl salicylate, Vertofix Coeur, Iso-E-Super, Fixolide NP, evernyl, iraldein gamma, phenylacetic acid, geranyl acetate, benzyl acetate, rose oxide, romilate, irotyl and floramate, by themselves or in mixtures, can be employed.

Dyestuffs which can be employed are the substances which are suitable and approved for cosmetic purposes, such as are summarized, for example, in the publication "Kosmetische Färbemittel [Cosmetic Coloring Agents]" of the Dyestuffs Commission of the Deutsche Forschungsgemeinschaft, Verlag Chemie, Weinheim, 1984, p. 81 to 106. These dyestuffs are conventionally employed in concentrations of from 0.001 to 0.1 wt. %, based on the total mixture.

Biogenic active compounds are to be understood as meaning, for example, tocopherol, tocopherol acetate, tocopherol palmitate, ascorbic acid, deoxyribonucleic acid, coenzyme Q10, retinol, bisabolol, allantoin, phytantriol, panthenol, AHA acids, amino acids, hyaluronic acid, alpha-hydroxy acids, polyglutamic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolysates, plant extracts, sphingolipids and vitamin complexes.

Care additive which the formulations can comprise are e.g. ethoxylated glycerol fatty acid esters, such as, for example, PEG-7 Glyceryl Cocoate, or cationic polymers, such as, for example, Polyquaternium-7 or polyglycerol esters.

Super-oiling agents which can be used are substances such as, for example, lanolin and lecithin and polyethoxylated or acylated lanolin and lecithin derivatives, polyol fatty acid esters, monoglycerides and fatty acid alkanolamides, the latter simultaneously serving as foam stabilizers.

Solvents which can be employed are e.g. aliphatic alcohols, such as ethanol, propanol or 1,3-propanediol, cyclic carbonates, such as ethylene carbonate, propylene carbonate, glycerol carbonate, esters of mono- or polycarboxylic acids, such as ethyl acetate, ethyl lactate, dimethyl adipate and diethyl adipate, propylene glycol, dipropylene glycol, glycerol, glycerol carbonate or water.

A further additional component which is preferably employed is the group of film-forming agents, in order to improve the water resistance of the compositions and therefore also to increase the UV protection performance. Film-forming agents which are preferably employed are polyurethanes, Dimethicone Copolyol, polyacrylates, PVP/VA copolymer (PVP=polyvinylpyrrolidone, VA=vinyl acetate), polyvinylpyrrolidone (PVP), copolymers of polyvinylpyrrolidone, PVP/hexadecene copolymer or PVP/eicosene copolymer.

A further additional component which is preferably employed is the group of deodorant and antiperspirant active compounds. From this group, astringents are preferably employed, particularly preferably basic aluminium chlorides, such as aluminium chlorohydrate ("ACH") or aluminium zirconium glycine salts ("ZAG").

The additional components might be added to the composition after finishing of step (c) of the method of the invention or during the performance of step (a), (b) and/or (c). Especially the addition of preservatives might be done while performing step (b) and/or (c). It is preferred to add the additional components into the dispersion obtained in step (c).

Compositions according to the invention can be used, for example, as a skin care, face care, head care, body care, intimate care, foot care, hair care, nail care, dental care or oral care product. Therefore the composition of the invention can be a personal care or cosmetic composition selected from a skin care, face care, head care, body care, intimate care, foot care, hair care, nail care, dental care or oral care compositions.

Compositions according to the invention can be used, for example, in the form of an emulsion, a suspension, a solution, a cream, an ointment, a paste, a gel, an oil, a powder, an aerosol, a stick, a spray, a cleansing product, a make-up or sunscreen preparation or a face lotion. Therefore the composition of the invention can be an emulsion, a suspension, a solution, a cream, an ointment, a paste, a gel, an oil, a powder, an aerosol, a stick, a spray, a cleansing product, a make-up or sunscreen preparation or a face lotion.

The compositions of the invention, preferably the cosmetic, dermatological or personal care compositions preferably comprise 0.1 to 60% by weight, preferably 0.5 to 25% by weight, more preferably 1 to 10% by weight and particularly preferably 2 to 5% by weight of the microbeads of the invention.

The microbeads of the invention or the composition of the invention or a dispersion obtained by a method according to the invention can be used for the manufacture of a moisturizer, a personal care, a hair care, a skin care or a cosmetic composition.

The microbeads of the invention or the composition of the invention or a dispersion obtained by a method according to the invention can especially be used as a topical dermal filler. The microbeads of the invention preferably congregate in wrinkles and folds of the skin. Therefore the products of the invention show many advantages when used for the preparation or as topical dermal filler. Special advantages are the reduction of the depth of wrinkles and the reduction of dermal roughness. The skin becomes more shiny and has a better radiance. Therefore another aspect of the invention is the use of microbeads of the invention or the composition of the invention or a dispersion obtained by a method according to the invention for the manufacture of topical dermal filler to treat wrinkles and rough skin.

The examples set out below describe the present invention by way of example, without the invention—whose scope for application is apparent from the entire description and the claims—being restricted to the embodiments specified in the examples.

EXAMPLES

Example 1

Preparation of Crosslinked Microparticles in Decylcocoate 70 g of a solution of 6% by weight of sodium hyaluronate (HyaCare®, Evonik Goldschmidt GmbH) in aqueous NaOH (0.2 M) was added in 2 minutes by vigorous stirring with a hand blender (SG Zauberstab, Typ M 122 2-Speed) at level 1 to a mixture of 27 g Decylcocoat (TEGOSOFT® DC, Evonik Goldschmidt GmbH) and 3 g Polyglyceryl-4 diisostearat/polyhydroxystearat/sebacat (ISOLAN® GPS, Evonik Goldschmidt GmbH). The resulting mixture was homogenized for 3 minutes with the hand blender at level 2. A solution of 512 µl Divinylsulfon in a mixture of 3 g decylcocoate and 5 ml ethanol was added by stirring to the homogenized mixture. The resulting emulsion was stirred for another 1.5 h. The pH was then regulated to a value of 9 by adding lactic acid (90% by weight in water) while stirring. The resulting product was a white dispersion.

Example 2

Preparation of Crosslinked Microparticles in Diethyl Hexylcarbonate

A solution of 4.2 g sodium hyaluronate (HyaCare®, Evonik Goldschmidt GmbH) in 66 g of an aqueous NaOH (0.2 M) was added in 2 minutes by vigorous stirring with a hand blender (level 1) to a mixture of 27 g Diethyl hexylcarbonate (TEGOSOFT® DEC, Evonik Goldschmidt GmbH) and 3 g Polyglyceryl-4 diisostearat/polyhydroxystearat/sebacat (ISOLAN® GPS, Evonik Goldschmidt GmbH). The resulting pre emulsion was homogenized for 2 minutes with the hand blender at level 2. A solution of 358 µl Divinylsulfon in 3 g diethyl hexylcarbonate was added drop-by-drop to the homogenized pre emulsion. The resulting mixture was stirred for another 0.5 h at a temperature of 50° C. The resulting product was a white dispersion.

A picture of the dispersion (FIG. 1) taken with a microscope shows clearly the spherical character of the microbeads (particles).

Figure 2:
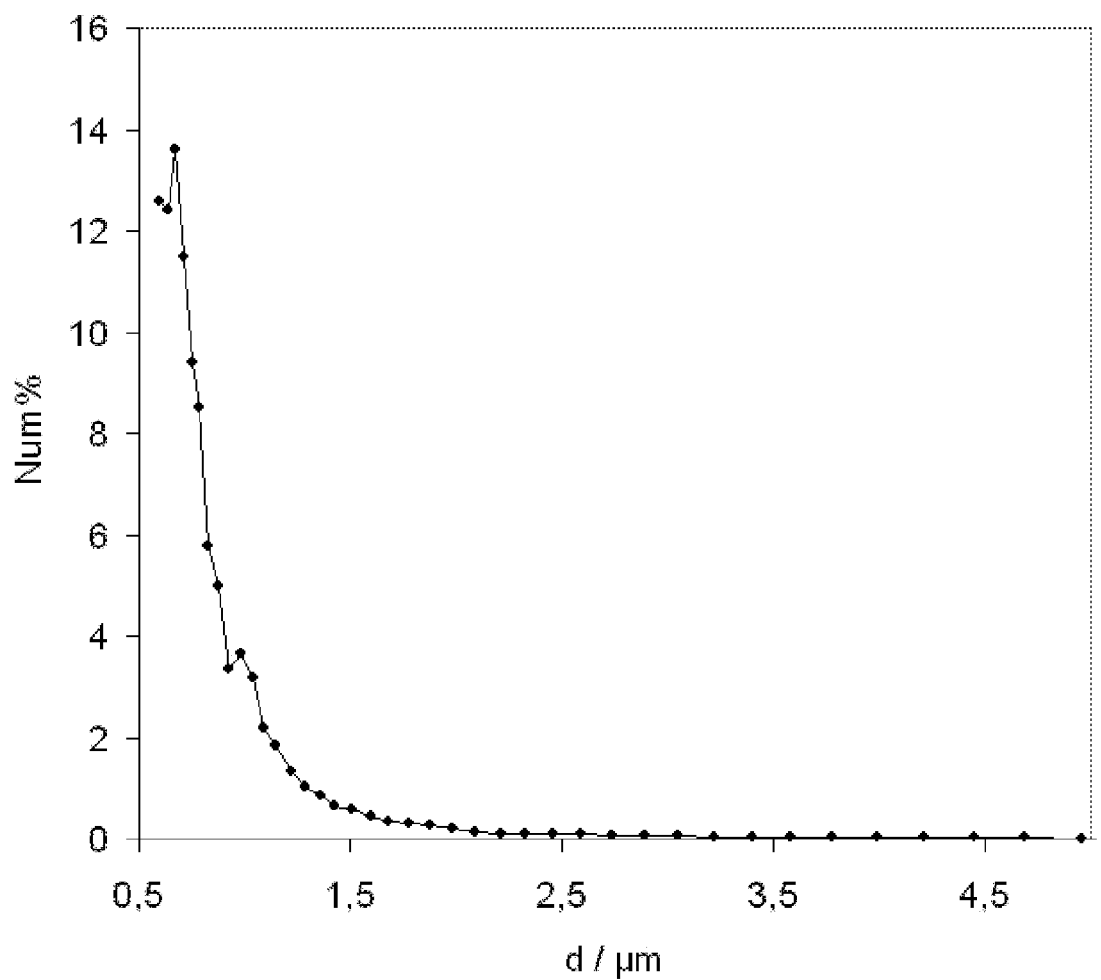

The particle size distribution was determined with an optical particle sizer (Accusizer, company: Particle Sizing Systems). The particle size distribution is shown in FIG. 2

Example 3

Preparation of a Dispersion of Crosslinked Microparticles in Decyl Cocoate Using PEG/PPG-10/1 Dimethicone as Emulsifier A solution of 5.9 g sodium hyaluronate (HyaCare®, Evonik Goldschmidt GmbH) in 92 g of an aqueous NaOH (0.2 M) was added in 2 minutes by vigorous stirring with a hand blender (level 1) to a mixture of 38.2 g Decylcocoate (TEGOSOFT® DC, Evonik Goldschmidt GmbH) and 4.2 g PEG/PPG-10/1 dimethicone (ABIL® EM 90, Evonik Goldschmidt GmbH). The resulting pre emulsion was homogenized for 2 minutes with the hand blender at level 2. A solution of 450 µl Divinylsulfon in 3.8 g decylcocoate was added drop-by-drop to the homogenized pre emulsion. The resulting mixture was stirred for another 0.5 h at room temperature. The resulting product was a white dispersion.

Example 4

Preparation of a Dispersion of Cross-Linked Microparticles in Diethyl Hexyl Carbonate Using Glyceryl Monooleate as Emulsifier The preparation was done according to example 2.3 g glyceryl monooleat (TEGIN® O V, Evonik Goldschmidt GmbH) were used instead of 3 g Polyglyceryl-4 diisostearat/polyhydroxystearat/sebacat.

Example 5

Preparation of Fluorescence Marked Crosslinked Microparticles of Sodium Hyaluronate A solution of 5.6 g sodium hyaluronate (HyaCare®, Evonik Goldschmidt GmbH) and 0.5 mg fluorescine in 88 g of an aqueous NaOH (0.2 M) was added in 2 minutes by vigorous stirring with a hand blender (level 1) to a mixture of 36 g diethyl hexylcarbonate (TEGOSOFT® DEC, Evonik Goldschmidt GmbH) and 4 g polyglyceryl-4 diisostearat/polyhydroxystearate/sebacate (ISOLAN® GPS, Evonik Goldschmidt GmbH). The resulting pre-emulsion was homogenized for 2 minutes with the hand blender at level 2. A solution of 486 µl Divinylsulfon in 4 g diethyl hexylcarbonate was added drop-by-drop to the homogenized pre-emulsion. The resulting mixture was stirred for another 0.5 h at a temperature of 50° C. The resulting product was a slightly green dispersion.

Example 6

Figure 3:
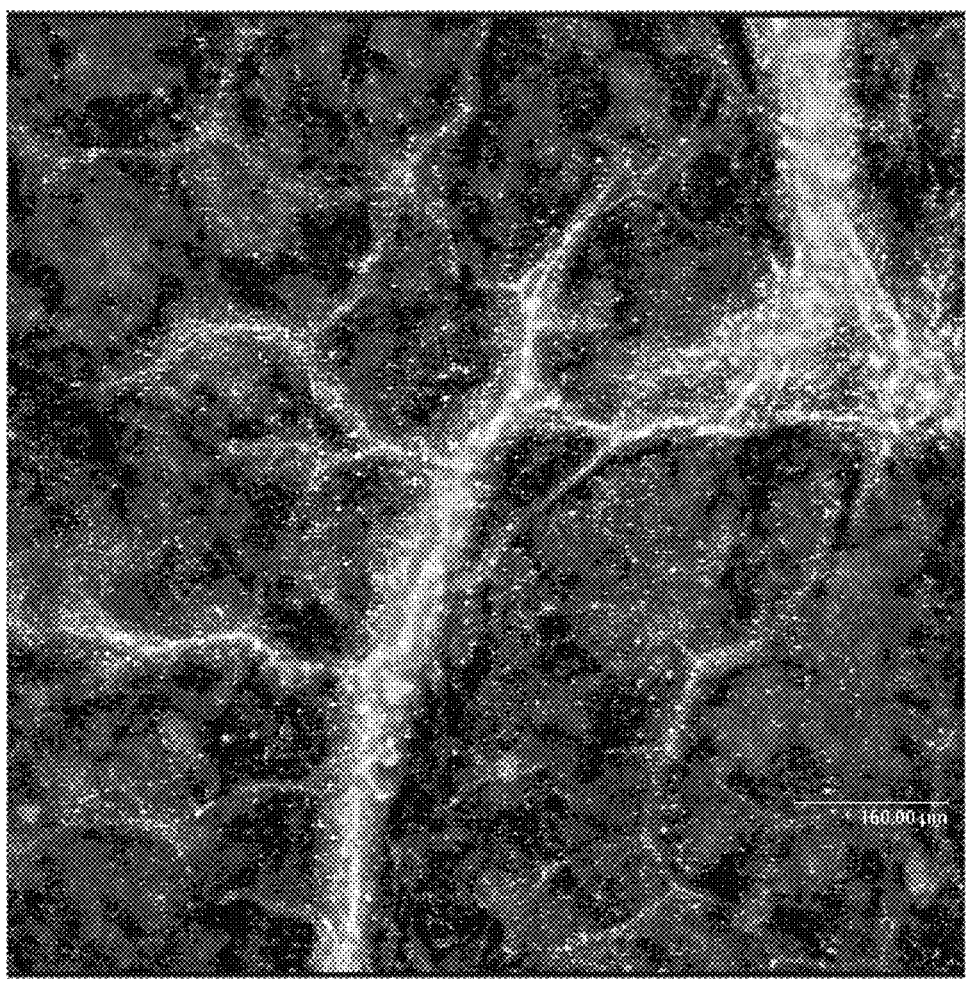

Application of a Dispersion of Cross-Linked Sodium Hyaluronate Microparticles to Pig Skin Approximately 2 cm$^2$ of a frozen pig skin were defreezed and shaved afterwards. 0.1 ml of the disperion of example 5 were dispersed to the pig skin using a spatula. The pig skin was examined with a fluorescence microscope (phase-contrast microscope, company: Leica, magnification 10×) afterwards. A photograph of this microscope picture is shown in FIG. 3. It can clearly be seen that the fluorescent particles accumulate in the skin wrinkles.

Example 7

Preparation of a Dispersion of Cross-Linked Microparticles Using Isostearic Acid for Neutralisation The preparation was done according to example 1. Isostearic acid (1% by weight based on the total weight of the dispersion) was used instead of lactic acid to adjust the pH. The resulting product was a white dispersion.

Example 8

Fluorescent Modification of Sodium Hyaluronate 10 g Sodium hyaluronate (HyaCare®) were suspended in 100 ml toluene. 0.025 g DTAF (5-(4,6-Dichloro-s-triazin-2-ylamino) fluorescein hydrochlorid, Sigma) were dissolved in 15 ml ethanol and this solution was added to the HyaCare® suspension. The suspension was stirred at room temperature for 16 h and filtered. The solid residue washed with ethanol and dried at reduced pressure.

Example 9

Preparation of the Fluorescently Marked Particle Dispersion 116 g of a 6% (by weight) solution of the fluorescent sodium hyaluronate of example 9 in 0.2 M NaOH were added to a mixture of 43.3 g decyl cocoate (TEGOSOFT® DC) and 4.8 g ISOLAN® GPS with stirring (hand blender, level 1). The emulsion was homogenized with the hand blender (level 2) for 3 min. 572 μg of divinylsulfone in a mixture of 4.8 g decyl cocoate and 5 ml ethanol were added to the emulsion with stirring. Stirring was continued for 1 h at room temperature, subsequently 8 g isostearic acid were added while stirring. The resulting dispersion had a pH of 9.

Example 10

Cosmetic Formulation Containing Ha Particles

The dispersion of fluorescently marked particles obtained in example 9 was formulated in a cosmetic cream. The composition (in % by weight) of this cream is given in table 1.

TABLE 1

Cosmetic cream composition comprising fluorescently marked particles.

| | | |
|---|---|---|
| TEGO ® Care 450 | Polyglyceryl-3 Methylglucose Distearate | 3.0% |
| TEGIN ® M Pellets | Glyceryl Stearate | 2.0% |
| TEGO ® Alkanol 18 | Stearyl Alcohol | 1.0% |
| TEGOSOFT ® OS | Ethylhexyl Stearate | 10.0% |
| TEGOSOFT ® DO | Decyl Oleate | 9.0% |
| Glycerin | | 3.0% |
| HA Particle Dispersion | | 3.0% |
| Microcare MEM | Methylisothiazolinone, Ethylparaben, Methylparaben | 0.8% |
| Water | | ad 100.0% |

Example 11

Cream Containing Crosslinked Hyaluronic Acid

A cream is produced containing 0.11% crosslinked Hyaluronic Acid (CL-HA) by mixing the following components (Table 2) while stirring:

TABLE 2

Cream composition of example 11 (% by weight)

| | |
|---|---|
| Polyglyceryl-3 Methylglucose Dioleate | 3.0% |
| Glyceryl Stearate | 2.0% |
| Stearyl Alcohol | 1.0% |
| Ethylhexyl Stearate | 9.5% |
| Caprylic/Capric Triglyceride | 9.5% |
| Water | 72.4% |
| Crosslinked HA Dispersion (Example 7) | 2.6% |

This formulation is applied on the inner forearm of 12 panelists. Before the application and after 2 and 7 hours a picture of the inner forearm is taken using a digital camera (Visioscan VC 98, Courage & Khazaka, Cologne, Germany). This picture is a digital black-and-white picture, which is divided into 256 grey levels. On the basis of the grey level distribution the software (coming with the Visioscan VC 98) calculates the different skin parameters like scaliness, roughness, surface, volume or texture parameters.

1. Skin Scaliness

Based on the grey level distribution the software calculates the proportion of light pixels to evaluate the parameter skin scaliness. The following table 3 shows the reduction of the scaliness.

TABLE 3

Results for skin scaliness in %

| | 2 h | 7 h |
|---|---|---|
| Control | −8.3% | −5.3% |
| Vehicle | −14.9% | −0.8% |
| CL-HA | −14.5% | −10.1% |

Figure 4:
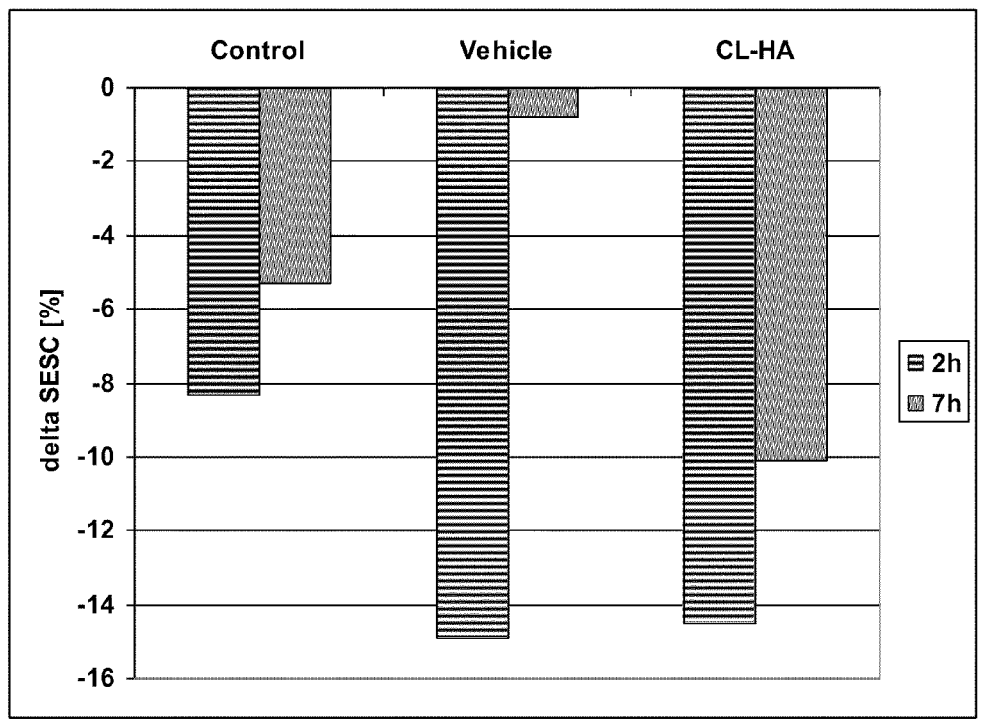
FIG. 4 to FIG. 7 show the skin parameters scaliness (FIG. 4), surface and volume (FIG. 5), roughness (FIG. 6), and texture (FIG. 7) as determined in Example 11.

Two hours after the application the control field (untreated) as well as the fields treated with vehicle or CL-HA show a reduction of skin scaliness. This effect decreases after 7 h on the control field and the vehicle treated field while the reduction of scaliness by CL-HA still persists after 7 h. A graph is given in FIG. 4 showing the results from the Skin Scaliness test.

2. Surface and Volume

The parameter Surface calculates the total surface of the skin. That means the lower the number of wrinkles or the smaller the wrinkles are the smaller the surface should be. The parameter Volume describes the volume necessary to fill the wrinkles. Both parameters will decrease if the depth and number of wrinkles is reduced by a test formulation. For this reason a sum of the change of both parameters after treatment with the test formulation is calculated:

$$\text{Sum}_{surf\text{-}vol} = \Delta\text{Surface} + \Delta\text{Volume [\%]}.$$

The results are given in table 4.

TABLE 4

Results for $\text{sum}_{surf\text{-}vol}$ in %

| | 2 h | 7 h |
|---|---|---|
| Control | 4.3% | 0.6% |
| Vehicle | −10.0% | 0.9% |
| CL-HA | −10.9% | −19.4% |

Figure 5:
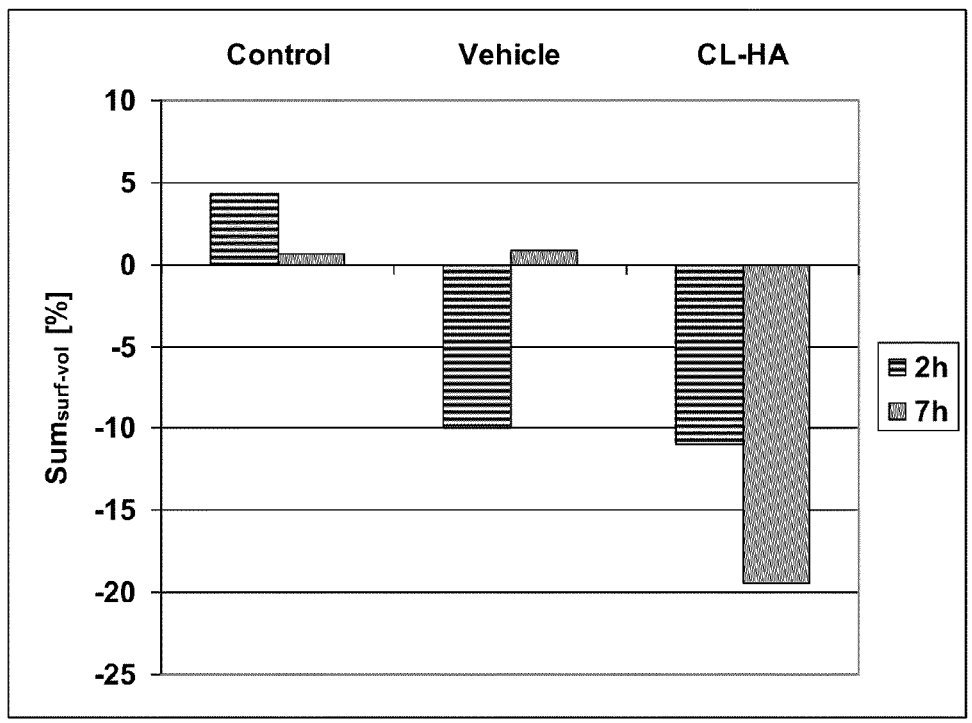

Two hours after application Surface and Volume are reduced by the vehicle and by the formulation containing CL-HA. After seven hours this positive effect disappears on the vehicle treated skin while the effect even improves on the test field treated with CL-HA. A graph is given in FIG. 5 showing the results from the surface and volume test.

3. Roughness Parameter R1-R5

The roughness parameters R1, R2, R3, R4 and R5 originate from the metal industry. They correspond to the roughness parameters Rt, Rm, Rz, Rp and Ra as defined in DIN 4762-4768. They describe the depth of deep and fine wrinkles. All roughness parameters will decrease if the depth of wrinkles is reduced. For this reason the parameters are summarized:

$$\text{Sum}_{R1\text{-}R5} = \Delta R1 + \Delta R2 + \Delta R3 + \Delta R4 + \Delta R5$$

The following table 5 shows the results for $\text{Sum}_{R1\text{-}R5}$.

TABLE 5

Results for $\text{Sum}_{R1\text{-}R5}$ in %

| | 2 h | 7 h |
|---|---|---|
| Control | 21.6% | 20.9% |
| Vehicle | −26.4% | −1.2% |
| CL-HA | −27.6% | −21.4% |

Figure 6:
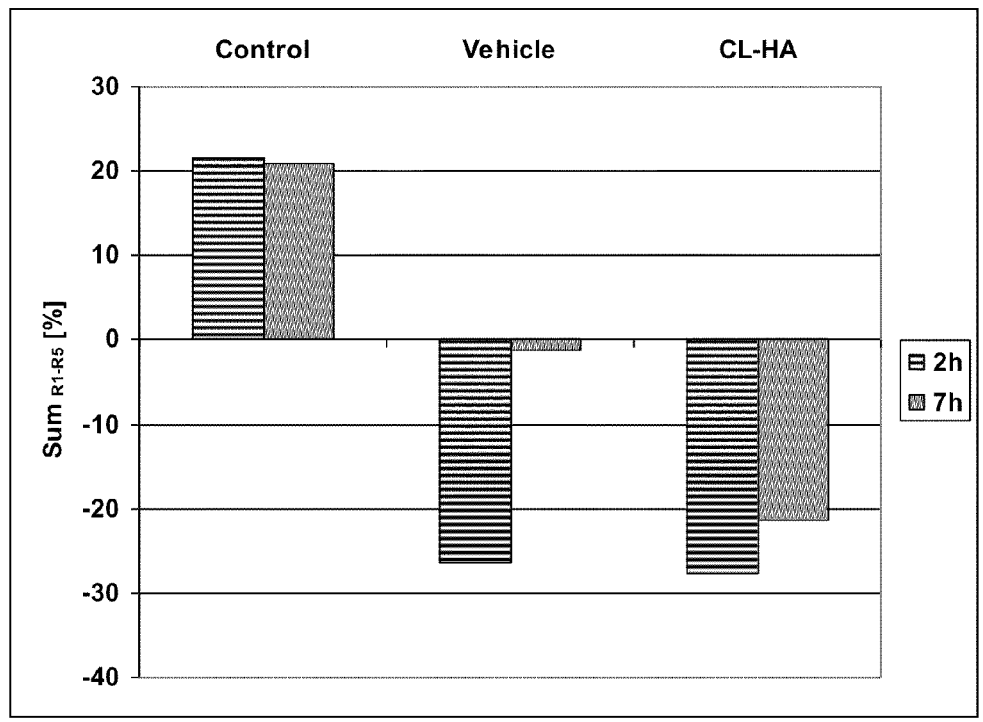

Two hours after application vehicle and the test formulation containing CL-HA reduce skin roughness. This effect disappears after seven hours on the vehicle treated test field while it remains nearly constant on the test field treated with CL-HA. A graph is given in FIG. 6 showing the results from the roughness parameter test.

4. Texture Parameters

The texture parameters (energy NRJ, entropy ENT, homogenity HOM, contrast CONT and variance VAR) refer to the color differences of neighboured pixels. They describe how even the skin tone is, that means an improvement of the texture parameters is linked with an improved skin appearance. This parameters are summarized using the following equation:

$$Sum_{tex-par.} = \Delta NRJ + \Delta ENT + \Delta HOM - \Delta CONT - \Delta VAR$$

The following table 6 shows the results for the $Sum_{tex-par.}$

TABLE 6

Results for the $Sum_{tex-par.}$ in %

|  | 2 h | 7 h |
|---|---|---|
| Control | −25.6% | 4.3% |
| Vehicle | 29.4% | 19.7% |
| CL-HA | 29.7% | 32.4% |

Figure 7:
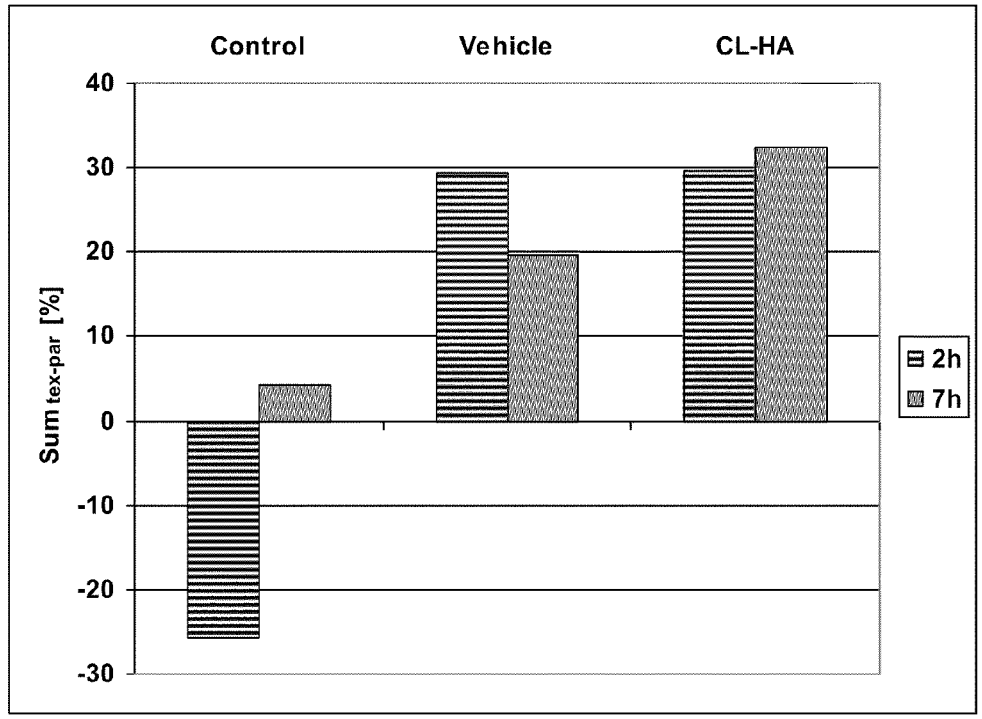

Two hours after application vehicle as well as the test formulation with CL-HA improve the texture parameters. On the test field treated with CL-HA this effect still persists after seven hours while it decreases on the skin treated with vehicle. A graph is given in FIG. 7 showing the results from texture Parameter test.

Thus, the microbeads of the invention are effective in reducing wrinkles and skin scaliness and in improving the skin's texture parameters leading to a more even skin tone.

The invention claimed is:

1. A method of producing crosslinked hyaluronic acid microbeads, said method comprising:
   (a) providing an aqueous alkaline solution comprising an alkali metal hydroxide and hyaluronic acid, or a salt thereof;
   (b) adding the aqueous solution from part (a) to an organic or oil phase to form a water in organic or water in oil (W/O) emulsion, wherein the amount of organic or oil phase used is from 20% to less than 50% by weight based on the sum of organic or oil phase and water; and
   (c) adding a solution comprising a crosslinking agent to the emulsion from part (b), wherein reaction of hyaluronic acid with the crosslinking agent takes place to provide crosslinked hyaluronic acid microbeads.

2. The method of claim 1, wherein the hyaluronic acid, or salt thereof, is recombinantly produced in a *Bacillus* host cell.

3. The method of claim 1, wherein the hyaluronic acid, or salt thereof, has an average molecular weight between 50 and 3,000 kDa.

4. The method of claim 1, wherein the aqueous alkaline solution comprises dissolved hyaluronic acid, or salt thereof, in a concentration between 0.1% to 40% (w/v).

5. The method of claim 1, wherein the aqueous alkaline solution comprises dissolved sodium hydroxide in a concentration between 0.001 to 2.0 M.

6. The method of claim 1, wherein the crosslinking agent is present in a weight ratio between 1:1 and 100:1 of hyaluronic acid or a salt thereof: crosslinking agent (dry weight).

7. The method of claim 1, wherein the oil or organic phase is an emollient for cosmetic or personal care formulations, with the proviso that the emollient is not a hydrocarbon, an aromatic hydrocarbon, and is not cetylethylhexanoate.

8. The method of claim 1, wherein the crosslinking agent is selected from divinylsulfone, glycerol diglycidyl ether and 1,4-butanediyl diglycidyl ether.

9. The method of claim 1, wherein the microdroplets have an average diameter from about 1 nanometer to 1 millimeter.

10. The method of claim 1, wherein in step (b) polyglyceryl-4-diisostearate/polyhydroxysterate/sebacate or PEG/PPG-10/1 dimethicone is used as an emulsifier.

11. The method of claim 1, further comprising:
    (d) working up the dispersion of crosslinked hyaluronic acid microbeads obtained in step (c).

12. The method of claim 1, wherein the amount of organic or oil phase used is from 25% to 45% by weight based on the sum of organic or oil phase and water.

13. The method of claim 12, wherein the amount of organic or oil phase used is from 30% to 40% by weight based on the sum of organic or oil phase and water.

14. The method of claim 1, wherein the crosslinking agent is present in a weight ratio between 2:1 and 50:1 of hyaluronic acid or a salt thereof: crosslinking agent (dry weight).

15. The method of claim 1, wherein said crosslinked hyaluronic acid microbeads have a degree of crosslinking of from 0.001 to 1.

16. The method of claim 1, wherein said crosslinked hyaluronic acid microbeads have a degree of crosslinking of from 0.01 to 0.5.

17. The method of claim 1, wherein said crosslinked hyaluronic acid microbeads have a size from 0.5 to 10 μm.

18. The method of claim 11, wherein step (d) comprises dialyzing the crosslinked microbeads against de-ionized water using a dialysis membrane that allows free diffusion of molecules having a size less than 13,000 Daltons.

19. The method of claim 11, wherein step (d) comprises neutralizing the pH of the crosslinked microbeads with a buffer or an acid to a pH of from 7.0 to 9.5.

20. A method of producing crosslinked hyaluronic acid microbeads, said method comprising:
    (a) providing an aqueous alkaline solution comprising an alkali metal hydroxide and hyaluronic acid, or a salt thereof;
    (b) adding the aqueous solution from part (a) to an oil phase to form a water in oil (W/O) emulsion, wherein the amount of oil phase used is from 25% to 45% by weight based on the sum of oil phase and water, and the oil or organic phase is an emollient for cosmetic or personal care formulations, with the proviso that the emollient is not a hydrocarbon, an aromatic hydrocarbon, and is not cetylethylhexanoate; and
    (c) adding a solution comprising a crosslinking agent to the emulsion from part (b), wherein reaction of hyaluronic acid with the crosslinking agent takes place to provide crosslinked hyaluronic acid microbeads.

* * * * *